US008974540B2

(12) United States Patent
Podolsky (10) Patent No.: US 8,974,540 B2
(45) Date of Patent: Mar. 10, 2015

(54) METHOD AND APPARATUS FOR ATTACHMENT IN A MODULAR HIP REPLACEMENT OR FRACTURE FIXATION DEVICE

(71) Applicant: iHip Surgical, LLC, Newport Beach, CA (US)

(72) Inventor: Anatol Podolsky, Corona Del Mar, CA (US)

(73) Assignee: iHip Surgical, LLC, Newport Beach, CA (US)

( * ) Notice: Subject to any disclaimer, the term of this patent is extended or adjusted under 35 U.S.C. 154(b) by 0 days.

(21) Appl. No.: 13/797,794

(22) Filed: Mar. 12, 2013

(65) Prior Publication Data

US 2013/0204390 A1    Aug. 8, 2013

Related U.S. Application Data

(60) Continuation-in-part of application No. 13/335,216, filed on Dec. 22, 2011, now Pat. No. 8,579,985, which is a continuation-in-part of application No. 13/049,619, filed on Mar. 16, 2011, now Pat. No.

(Continued)

(51) Int. Cl.
*A61F 2/32* (2006.01)
*A61F 2/36* (2006.01)

(Continued)

(52) U.S. Cl.
CPC ............. *A61F 2/3609* (2013.01); *A61F 2/4637* (2013.01); *A61F 2002/30332* (2013.01);

(Continued)

(58) Field of Classification Search
CPC ............ A61F 2002/30408; A61F 2002/30332; A61F 2002/30339; A61F 2002/30334; A61F 2002/30327; A61F 2002/30329
USPC ........................ 623/22.4–22.46, 20.32–20.36, 623/19.11–19.14
See application file for complete search history.

(56) References Cited

U.S. PATENT DOCUMENTS 2,612,159 A    9/1952    Collison
2,679,245 A    5/1954    Timmermans (Continued)

FOREIGN PATENT DOCUMENTS

CN    201150576 Y    12/2007
DE    2620907    11/1977

(Continued)

OTHER PUBLICATIONS

Cooper et al., Corrosion at the Head-Neck Taper as a Cause for Adverse Local Tissue Reactions After Total Hip Arthroplasty, J Bone Joint Surg Am. 2012;94:1655-61 dated Sep. 12, 2012.

(Continued)

*Primary Examiner* — Alvin Stewart
(74) *Attorney, Agent, or Firm* — James W. Hill; Mark Bentley; McDermott Will & Emery LLP (57) ABSTRACT

Methods and apparatus for orthopedic replacement of the hip and hip fracture fixation devices include structures and techniques for fixing or enhancing interconnection of implant components, such as by increasing the interconnection in an interference fit with one or more tapers, threads, and/or cooling of components prior to assembly. For example, a prosthetic femoral neck implant can include a thread and a Morse taper for lockable attachment to a prosthetic femoral head and/or intramedullary stem.

10 Claims, 5 Drawing Sheets

Related U.S. Application Data 8,211,183, which is a division of application No. 12/518,081, filed as application No. PCT/US2006/046795 on Dec. 7, 2006, now Pat. No. 8,029,573.

(60) Provisional application No. 61/722,960, filed on Nov. 6, 2012.

(51) Int. Cl.
  *A61F 2/46* (2006.01)
  *A61F 2/30* (2006.01)

(52) U.S. Cl.
  CPC . *A61F2002/30405* (2013.01); *A61F 2002/365* (2013.01); *A61F 2002/3652* (2013.01); *A61F 2002/30334* (2013.01); *A61F 2002/30367* (2013.01); *A61F 2002/4653* (2013.01)
  USPC .................................................. 623/22.4

(56) References Cited

U.S. PATENT DOCUMENTS

| | | | |
|---|---|---|---|
| 2,682,265 A | 6/1954 | Collison | |
| 2,718,228 A | 9/1955 | Van Steenbrugghe | |
| 2,719,522 A * | 10/1955 | Hudack | 623/23.15 |
| 2,781,758 A | 2/1957 | Chevalier | |
| 2,785,673 A | 3/1957 | Anderson | |
| 2,947,308 A | 8/1960 | Gorman | |
| 3,064,645 A | 11/1962 | Ficat et al. | |
| 3,067,740 A | 12/1962 | Haboush | |
| 3,102,536 A * | 9/1963 | Rose et al. | 623/22.4 |
| 3,466,670 A * | 9/1969 | Christiansen | 623/22.43 |
| 3,512,184 A | 5/1970 | Groove | |
| 3,530,854 A | 9/1970 | Kearney | |
| 3,605,123 A | 9/1971 | Hahn | |
| 3,656,184 A | 4/1972 | Chambers | |
| 3,658,056 A * | 4/1972 | Huggler et al. | 623/22.43 |
| 3,683,421 A | 8/1972 | Martinie | |
| 3,806,957 A | 4/1974 | Shersher | |
| 3,829,904 A | 8/1974 | Ling et al. | |
| 3,848,272 A | 11/1974 | Noiles | |
| 3,859,669 A | 1/1975 | Shersher | |
| 3,875,593 A | 4/1975 | Shersher | |
| 3,896,505 A | 7/1975 | Timmermans | |
| 3,903,549 A | 9/1975 | Deyerle | |
| 3,906,550 A | 9/1975 | Rostoker et al. | |
| 3,918,441 A | 11/1975 | Getscher | |
| 3,939,497 A | 2/1976 | Heimke et al. | |
| 3,943,576 A | 3/1976 | Sivash | |
| 3,978,528 A | 9/1976 | Crep | |
| 3,987,499 A * | 10/1976 | Scharbach et al. | 623/17.11 |
| 4,012,795 A * | 3/1977 | Dorre et al. | 623/22.46 |
| 4,016,651 A | 4/1977 | Kawahara et al. | |
| 4,021,865 A | 5/1977 | Charnley | |
| 4,051,559 A | 10/1977 | Pifferi | |
| 4,060,472 A * | 11/1977 | Alewitz | 204/196.16 |
| 4,080,666 A | 3/1978 | Fixel | |
| 4,086,701 A | 5/1978 | Kawahara et al. | |
| 4,089,071 A | 5/1978 | Kalnberz et al. | |
| 4,101,985 A | 7/1978 | Baumann et al. | |
| 4,115,875 A * | 9/1978 | Rambert et al. | 623/22.46 |
| 4,129,903 A | 12/1978 | Huggler | |
| 4,172,452 A | 10/1979 | Forte et al. | |
| 4,198,711 A * | 4/1980 | Zeibig | 623/22.43 |
| 4,225,981 A * | 10/1980 | Zeibig | 623/22.43 |
| 4,259,072 A | 3/1981 | Hirabayashi et al. | |
| 4,282,618 A * | 8/1981 | Wagner | 470/185 |
| 4,298,993 A | 11/1981 | Kovaleva et al. | |
| 4,304,110 A | 12/1981 | Fain | |
| 4,318,191 A | 3/1982 | Tepic | |
| 4,385,405 A | 5/1983 | Teinturier | |
| 4,404,691 A | 9/1983 | Buning et al. | |
| 4,432,358 A | 2/1984 | Fixel | |
| 4,488,319 A | 12/1984 | Von Recüm | |
| 4,520,511 A * | 6/1985 | Gianezio et al. | 623/22.46 |
| 4,530,114 A | 7/1985 | Tepic | |
| 4,532,660 A | 8/1985 | Field | |
| 4,532,661 A | 8/1985 | Halpern | |
| 4,578,081 A | 3/1986 | Harder et al. | |
| 4,608,055 A * | 8/1986 | Morrey et al. | 623/22.46 |
| 4,619,659 A | 10/1986 | Witzel | |
| 4,624,673 A | 11/1986 | Meyer | |
| 4,629,280 A * | 12/1986 | Semmler et al. | 439/87 |
| 4,630,601 A | 12/1986 | Harder et al. | |
| 4,676,797 A | 6/1987 | Anapliotis et al. | |
| 4,687,487 A | 8/1987 | Hintermann | |
| 4,693,724 A | 9/1987 | Rhenter et al. | |
| 4,709,854 A | 12/1987 | Biagini et al. | |
| 4,712,541 A | 12/1987 | Harder et al. | |
| 4,714,471 A | 12/1987 | Grundei | |
| 4,714,478 A | 12/1987 | Fischer | |
| 4,719,074 A * | 1/1988 | Tsuno et al. | 419/5 |
| 4,728,330 A | 3/1988 | Comparetto | |
| 4,728,334 A | 3/1988 | Spotorno | |
| 4,733,654 A | 3/1988 | Marino | |
| 4,752,295 A | 6/1988 | Frey et al. | |
| 4,752,296 A | 6/1988 | Buechel et al. | |
| 4,776,330 A | 10/1988 | Chapman et al. | |
| 4,795,473 A | 1/1989 | Grimes | |
| 4,822,368 A | 4/1989 | Collier | |
| 4,822,370 A * | 4/1989 | Schelhas | 623/22.46 |
| 4,823,366 A | 4/1989 | Williams | |
| 4,827,917 A | 5/1989 | Brumfield | |
| 4,834,756 A | 5/1989 | Kenna | |
| 4,842,606 A | 6/1989 | Kranz et al. | |
| 4,846,839 A | 7/1989 | Noiles | |
| 4,851,007 A | 7/1989 | Gray | |
| 4,871,369 A | 10/1989 | Muller | |
| 4,878,917 A | 11/1989 | Kranz et al. | |
| 4,895,571 A | 1/1990 | Grundei | |
| 4,904,264 A | 2/1990 | Scheunemann | |
| 4,908,032 A | 3/1990 | Keller | |
| 4,917,530 A | 4/1990 | Engelhardt et al. | |
| 4,919,673 A | 4/1990 | Willert et al. | |
| 4,919,678 A | 4/1990 | Kranz | |
| 4,919,679 A | 4/1990 | Averill et al. | |
| 4,921,500 A * | 5/1990 | Averill et al. | 623/22.45 |
| 4,936,853 A | 6/1990 | Fabian et al. | |
| 4,938,773 A | 7/1990 | Strand | |
| 4,944,764 A | 7/1990 | Stossel | |
| 4,946,459 A | 8/1990 | Bradshaw et al. | |
| 4,946,461 A | 8/1990 | Fischer | |
| 4,957,510 A * | 9/1990 | Cremascoli | 623/22.46 |
| 4,963,155 A | 10/1990 | Lazzeri et al. | |
| 4,976,740 A | 12/1990 | Kleiner | |
| 4,978,349 A | 12/1990 | Frigg | |
| 4,978,357 A | 12/1990 | Goymann et al. | |
| 4,985,037 A | 1/1991 | Petersen | |
| 4,994,085 A | 2/1991 | Sawai et al. | |
| 4,995,883 A | 2/1991 | Demane et al. | |
| 4,998,937 A | 3/1991 | Grimes | |
| 5,002,578 A | 3/1991 | Luman | |
| 5,002,581 A | 3/1991 | Paxson et al. | |
| 5,007,935 A | 4/1991 | Vincent et al. | |
| 5,019,108 A | 5/1991 | Bertin et al. | |
| 5,021,062 A | 6/1991 | Adrey et al. | |
| 5,026,280 A | 6/1991 | Dürr et al. | |
| 5,032,125 A | 7/1991 | Durham et al. | |
| 5,032,130 A * | 7/1991 | Schelhas et al. | 623/22.42 |
| 5,035,712 A | 7/1991 | Hoffman | |
| 5,037,438 A | 8/1991 | Davidson | |
| 5,037,441 A * | 8/1991 | Bouvet | 623/22.43 |
| 5,047,033 A | 9/1991 | Fallin | |
| 5,047,060 A * | 9/1991 | Henssge et al. | 623/22.46 |
| 5,058,936 A | 10/1991 | Kapgan et al. | |
| 5,080,676 A | 1/1992 | May | |
| 5,080,677 A * | 1/1992 | Shelley | 623/22.24 |
| 5,080,685 A * | 1/1992 | Bolesky et al. | 623/22.42 |
| 5,087,260 A | 2/1992 | Fixel | |
| 5,100,407 A | 3/1992 | Conrad et al. | |
| 5,108,437 A | 4/1992 | Kenna | |
| 5,108,451 A | 4/1992 | Forte | |
| 5,108,452 A | 4/1992 | Fallin et al. | |
| 5,116,379 A | 5/1992 | McLardy-Smith | |

(56) References Cited

U.S. PATENT DOCUMENTS

| | | |
|---|---|---|
| 5,123,926 A | 6/1992 | Pisharodi |
| 5,133,760 A | 7/1992 | Petersen et al. |
| 5,133,771 A | 7/1992 | Duncan et al. |
| 5,133,772 A | 7/1992 | Hack et al. |
| 5,135,529 A | 8/1992 | Paxson et al. |
| 5,139,424 A | 8/1992 | Yli-Urpo |
| 5,152,796 A | 10/1992 | Slamin |
| 5,152,798 A | 10/1992 | Kranz |
| 5,156,624 A * | 10/1992 | Barnes ........................ 623/22.45 |
| 5,156,626 A | 10/1992 | Broderick et al. |
| 5,163,961 A | 11/1992 | Harwin |
| 5,167,663 A | 12/1992 | Brumfield |
| 5,181,928 A | 1/1993 | Bolesky et al. |
| 5,190,546 A | 3/1993 | Jervis |
| 5,193,679 A | 3/1993 | White |
| 5,194,066 A | 3/1993 | Van Zile |
| 5,197,720 A | 3/1993 | Renz et al. |
| 5,197,988 A | 3/1993 | Spotorno et al. |
| 5,197,989 A | 3/1993 | Hinckfuss et al. |
| 5,201,769 A | 4/1993 | Schutzer |
| 5,201,882 A | 4/1993 | Paxson |
| 5,211,666 A | 5/1993 | Fetto |
| 5,217,499 A | 6/1993 | Shelley |
| 5,222,984 A | 6/1993 | Forte |
| 5,259,249 A | 11/1993 | Fetto |
| 5,286,260 A | 2/1994 | Bolesky et al. |
| 5,312,406 A | 5/1994 | Brumfield |
| 5,314,479 A | 5/1994 | Rockwood, Jr. et al. |
| 5,330,536 A | 7/1994 | Tager et al. |
| 5,336,268 A | 8/1994 | Rispeter |
| 5,342,366 A | 8/1994 | Whiteside et al. |
| 5,344,457 A | 9/1994 | Pilliar et al. |
| 5,360,238 A | 11/1994 | Godfrey et al. |
| 5,362,311 A * | 11/1994 | Amino et al. ............... 623/22.45 |
| 5,365,661 A * | 11/1994 | Mizuno et al. .............. 29/889.21 |
| 5,370,706 A * | 12/1994 | Bolesky et al. ............. 623/23.44 |
| 5,376,124 A | 12/1994 | Gustke et al. |
| 5,376,125 A | 12/1994 | Winkler |
| 5,376,126 A | 12/1994 | Lin |
| 5,389,107 A | 2/1995 | Nassar et al. |
| 5,390,683 A | 2/1995 | Pisharodi |
| 5,407,494 A * | 4/1995 | Post ............................ 148/521 |
| 5,413,610 A * | 5/1995 | Amino et al. ............... 623/22.43 |
| 5,454,813 A | 10/1995 | Lawes |
| 5,458,654 A | 10/1995 | Tepic |
| 5,480,451 A * | 1/1996 | Grundei et al. ............. 623/22.43 |
| 5,489,309 A | 2/1996 | Lackey et al. |
| 5,489,311 A | 2/1996 | Cipolletti |
| 5,507,817 A | 4/1996 | Craig et al. |
| 5,507,825 A | 4/1996 | Frei |
| 5,507,826 A | 4/1996 | Besselink et al. |
| 5,507,830 A | 4/1996 | DeMane et al. |
| 5,514,182 A * | 5/1996 | Shea ............................ 623/23.4 |
| 5,531,748 A | 7/1996 | De la Caffiniere |
| 5,549,703 A * | 8/1996 | Daigle et al. ............... 623/22.43 |
| 5,549,704 A | 8/1996 | Sutter |
| 5,549,706 A | 8/1996 | McCarthy |
| 5,562,666 A | 10/1996 | Brumfield |
| 5,569,263 A * | 10/1996 | Hein ............................ 606/102 |
| 5,571,203 A | 11/1996 | Masini |
| 5,580,247 A | 12/1996 | Gittleman |
| 5,580,352 A * | 12/1996 | Sekel .......................... 623/22.46 |
| 5,584,695 A | 12/1996 | Lal Sachdeva et al. |
| 5,591,233 A * | 1/1997 | Kelman et al. ............. 623/23.51 |
| 5,593,451 A | 1/1997 | Averill et al. |
| 5,597,378 A | 1/1997 | Jervis |
| 5,624,445 A | 4/1997 | Burke |
| 5,645,600 A | 7/1997 | Bimman |
| 5,645,607 A | 7/1997 | Hickey |
| 5,653,765 A | 8/1997 | McTighe et al. |
| 5,672,284 A | 9/1997 | Devanathan et al. |
| 5,697,932 A | 12/1997 | Smith et al. |
| 5,702,480 A | 12/1997 | Kropf et al. |
| 5,702,483 A | 12/1997 | Kwong |
| 5,713,902 A | 2/1998 | Friedl |
| 5,725,592 A * | 3/1998 | White et al. ................ 623/23.35 |
| 5,725,595 A | 3/1998 | Gustilo |
| 5,725,597 A | 3/1998 | Hwang |
| 5,728,128 A | 3/1998 | Crickenberger et al. |
| 5,735,905 A * | 4/1998 | Parr ............................ 623/23.11 |
| 5,741,262 A | 4/1998 | Albrektsson et al. |
| 5,755,807 A | 5/1998 | Anstaett et al. |
| 5,755,810 A | 5/1998 | Cunningham |
| 5,766,262 A | 6/1998 | Mikhail |
| 5,766,263 A | 6/1998 | Grundei et al. |
| 5,776,200 A | 7/1998 | Johnson et al. |
| 5,782,921 A | 7/1998 | Colleran et al. |
| 5,800,553 A * | 9/1998 | Albrektsson et al. ........ 623/22.4 |
| 5,800,554 A * | 9/1998 | Scholz ........................ 623/22.43 |
| 5,800,557 A | 9/1998 | Elhami |
| 5,817,098 A | 10/1998 | Albrektsson et al. |
| 5,865,850 A * | 2/1999 | Matthews ................... 623/22.43 |
| 5,871,547 A | 2/1999 | Abouaf et al. |
| 5,876,446 A | 3/1999 | Agrawal et al. |
| 5,876,459 A | 3/1999 | Powell |
| 5,879,407 A | 3/1999 | Waggener |
| 5,888,206 A * | 3/1999 | Lob et al. ................... 623/18.11 |
| 5,888,208 A | 3/1999 | Ro |
| 5,902,303 A | 5/1999 | Eckhof et al. |
| 5,902,340 A * | 5/1999 | White et al. ................. 128/898 |
| 5,904,720 A | 5/1999 | Farrar et al. |
| 5,906,644 A | 5/1999 | Powell |
| 5,928,235 A | 7/1999 | Friedl |
| 5,931,871 A | 8/1999 | Baur et al. |
| 5,961,555 A | 10/1999 | Huebner |
| 5,972,032 A | 10/1999 | Lopez et al. |
| 5,980,575 A | 11/1999 | Albrektsson et al. |
| 5,997,582 A | 12/1999 | Weiss |
| 6,010,535 A | 1/2000 | Shah |
| 6,045,555 A | 4/2000 | Smith et al. |
| 6,059,830 A | 5/2000 | Lippincott, III et al. |
| 6,067,701 A * | 5/2000 | Vandewalle ..................... 29/558 |
| 6,074,424 A | 6/2000 | Perrone, Jr. et al. |
| 6,102,953 A | 8/2000 | Huebner |
| 6,126,661 A | 10/2000 | Faccioli et al. |
| 6,126,691 A | 10/2000 | Kasra et al. |
| 6,136,036 A | 10/2000 | Scholz |
| 6,139,552 A | 10/2000 | Horiuchi |
| 6,142,998 A | 11/2000 | Smith et al. |
| 6,156,069 A | 12/2000 | Amstutz |
| 6,165,177 A | 12/2000 | Wilson et al. |
| 6,165,223 A | 12/2000 | Metzger et al. |
| 6,168,627 B1 | 1/2001 | Huebner |
| 6,168,628 B1 | 1/2001 | Chernyshov et al. |
| 6,187,049 B1 * | 2/2001 | Fujikawa et al. ............. 623/22.4 |
| 6,190,416 B1 * | 2/2001 | Choteau et al. ............ 623/22.12 |
| 6,193,758 B1 | 2/2001 | Huebner |
| 6,197,062 B1 * | 3/2001 | Fenlin ........................ 623/19.12 |
| 6,197,063 B1 | 3/2001 | Dews |
| 6,197,065 B1 | 3/2001 | Martin et al. |
| 6,214,052 B1 | 4/2001 | Burkinshaw |
| 6,221,074 B1 | 4/2001 | Cole et al. |
| 6,224,601 B1 | 5/2001 | Friedl |
| 6,228,086 B1 | 5/2001 | Wahl et al. |
| 6,228,121 B1 | 5/2001 | Khalili |
| 6,231,611 B1 | 5/2001 | Mosseri |
| 6,235,031 B1 | 5/2001 | Hodgeman et al. |
| 6,238,435 B1 | 5/2001 | Meulink et al. |
| 6,248,095 B1 | 6/2001 | Giambattista et al. |
| 6,248,112 B1 | 6/2001 | Gambale et al. |
| 6,261,290 B1 | 7/2001 | Friedl |
| 6,264,699 B1 * | 7/2001 | Noiles et al. ............... 623/23.23 |
| 6,277,082 B1 | 8/2001 | Gambale |
| 6,284,002 B1 | 9/2001 | Sotereanos |
| 6,299,648 B1 * | 10/2001 | Doubler et al. ............. 623/23.18 |
| 6,309,395 B1 | 10/2001 | Smith et al. |
| 6,319,286 B1 | 11/2001 | Fernandez et al. |
| 6,330,845 B1 | 12/2001 | Meulink |
| 6,355,068 B1 | 3/2002 | Doubler et al. |
| 6,371,991 B1 | 4/2002 | Manasas et al. |
| 6,379,360 B1 | 4/2002 | Ackeret et al. |
| 6,379,388 B1 | 4/2002 | Ensign et al. |
| 6,383,225 B2 * | 5/2002 | Masini ........................ 623/22.42 |
| 6,383,227 B1 | 5/2002 | Baroud et al. |

(56) References Cited

U.S. PATENT DOCUMENTS

| | | |
|---|---|---|
| 6,409,730 B1 | 6/2002 | Green et al. |
| 6,409,768 B1 | 6/2002 | Tepic et al. |
| 6,423,066 B1 | 7/2002 | Harder et al. |
| 6,428,578 B2 | 8/2002 | White |
| 6,432,110 B1 | 8/2002 | Richelsoph |
| 6,432,126 B1 | 8/2002 | Gambale et al. |
| 6,432,141 B1 | 8/2002 | Stocks et al. |
| 6,440,171 B1 | 8/2002 | Doubler et al. |
| 6,443,954 B1 | 9/2002 | Bramlet et al. |
| 6,458,092 B1 | 10/2002 | Gambale et al. |
| 6,464,728 B1 * | 10/2002 | Murray ................. 623/22.42 |
| 6,468,278 B1 | 10/2002 | Muckter |
| 6,479,565 B1 | 11/2002 | Stanley |
| 6,482,237 B2 | 11/2002 | Mosseri |
| 6,494,913 B1 | 12/2002 | Huebner |
| 6,494,918 B1 * | 12/2002 | Pope et al. ................. 623/23.6 |
| 6,503,252 B2 | 1/2003 | Hansson |
| 6,503,255 B1 | 1/2003 | Albrektsson et al. |
| 6,508,841 B2 | 1/2003 | Martin et al. |
| 6,517,541 B1 | 2/2003 | Sesic |
| 6,524,342 B1 | 2/2003 | Muhlhausler et al. |
| 6,607,561 B2 | 8/2003 | Brannon |
| 6,610,095 B1 | 8/2003 | Pope et al. |
| 6,616,697 B2 * | 9/2003 | Sotereanos ............. 623/23.26 |
| 6,620,170 B1 | 9/2003 | Ahern |
| 6,648,889 B2 | 11/2003 | Bramlet et al. |
| 6,656,187 B1 | 12/2003 | Camino |
| 6,682,568 B2 | 1/2004 | Despres, III et al. |
| 6,692,520 B1 | 2/2004 | Gambale et al. |
| 6,692,530 B2 | 2/2004 | Doubler et al. |
| 6,695,850 B2 | 2/2004 | Diaz |
| 6,695,883 B2 * | 2/2004 | Crofford ................ 623/22.46 |
| 6,699,293 B2 | 3/2004 | White |
| 6,702,854 B1 | 3/2004 | Cheal et al. |
| 6,706,072 B2 | 3/2004 | Dwyer et al. |
| 6,706,073 B2 | 3/2004 | Draenert et al. |
| 6,709,425 B2 | 3/2004 | Gambale et al. |
| 6,712,855 B2 | 3/2004 | Martin et al. |
| 6,719,805 B1 | 4/2004 | Ahern |
| 6,723,129 B2 | 4/2004 | Dwyer et al. |
| 6,755,862 B2 | 6/2004 | Keynan |
| 6,755,865 B2 | 6/2004 | Tarabishy |
| 6,758,864 B2 | 7/2004 | Storer et al. |
| 6,764,108 B2 * | 7/2004 | Ernst et al. .................. 285/333 |
| 6,786,929 B2 | 9/2004 | Gambale et al. |
| 6,800,095 B1 | 10/2004 | Pope et al. |
| 6,802,858 B2 | 10/2004 | Gambale et al. |
| 6,843,806 B2 | 1/2005 | Hayes, Jr. et al. |
| 6,851,160 B2 | 2/2005 | Carver |
| 6,866,683 B2 | 3/2005 | Gerbec et al. |
| 6,875,239 B2 | 4/2005 | Gerbec et al. |
| 6,887,276 B2 * | 5/2005 | Gerbec et al. ............ 623/18.11 |
| 6,902,583 B2 * | 6/2005 | Gerbec et al. ............ 623/23.47 |
| 6,905,502 B2 | 6/2005 | Penenberg |
| 6,913,623 B1 | 7/2005 | Zhu |
| 6,949,117 B2 | 9/2005 | Gambale et al. |
| 6,953,479 B2 * | 10/2005 | Carson et al. ............. 623/20.15 |
| 6,969,406 B2 * | 11/2005 | Tornier ..................... 623/19.13 |
| 6,974,483 B2 * | 12/2005 | Murray .................... 623/22.42 |
| 6,976,999 B2 | 12/2005 | Charlebois et al. |
| 6,986,790 B2 * | 1/2006 | Ball et al. ................ 623/19.11 |
| 6,988,784 B2 | 1/2006 | Silverbrook |
| 6,991,656 B2 | 1/2006 | Mears |
| 7,004,972 B2 | 2/2006 | Yoon |
| 7,033,399 B2 * | 4/2006 | Doubler et al. ........... 623/22.42 |
| 7,044,974 B2 * | 5/2006 | Garber et al. ............. 623/22.21 |
| 7,044,975 B2 | 5/2006 | Cheal et al. |
| 7,097,664 B2 | 8/2006 | Despres, III et al. |
| 7,104,995 B2 * | 9/2006 | Crofford ...................... 606/81 |
| 7,135,044 B2 * | 11/2006 | Bassik et al. ............. 623/22.42 |
| 7,141,073 B2 | 11/2006 | May et al. |
| 7,156,879 B1 * | 1/2007 | Albrektsson et al. ...... 623/23.14 |
| 7,169,184 B2 * | 1/2007 | Dalla Pria ................ 623/19.12 |
| 7,179,297 B2 | 2/2007 | McLean |
| 7,211,113 B2 | 5/2007 | Zelener et al. |
| 7,235,106 B2 * | 6/2007 | Daniels et al. ............ 623/22.42 |
| 7,247,171 B2 | 7/2007 | Sotereanos |
| 7,255,716 B2 | 8/2007 | Pubols et al. |
| 7,273,499 B2 | 9/2007 | McCleary et al. |
| 7,297,166 B2 | 11/2007 | Dwyer et al. |
| 7,306,600 B2 | 12/2007 | Roth et al. |
| 7,455,673 B2 | 11/2008 | Gotfried |
| 7,468,078 B2 | 12/2008 | Sederholm et al. |
| 7,494,509 B1 | 2/2009 | Hershberger et al. |
| 7,503,919 B2 | 3/2009 | Shaw |
| 7,520,947 B2 | 4/2009 | Kennedy et al. |
| 7,527,627 B2 | 5/2009 | Ferrante et al. |
| 7,569,075 B2 | 8/2009 | Johnson et al. |
| 7,572,294 B2 | 8/2009 | Meridew et al. |
| 7,582,092 B2 | 9/2009 | Jones et al. |
| D601,701 S | 10/2009 | Gotfried |
| 7,608,109 B2 * | 10/2009 | Dalla Pria ................ 623/19.11 |
| 7,608,112 B1 | 10/2009 | Kuczynski et al. |
| 7,655,162 B2 | 2/2010 | Kumar |
| 7,695,474 B2 | 4/2010 | Crofford |
| 7,695,521 B2 | 4/2010 | Ely et al. |
| 7,753,961 B2 | 7/2010 | Chen et al. |
| 7,766,968 B2 | 8/2010 | Sweeney |
| 7,776,098 B2 * | 8/2010 | Murphy .................... 623/22.42 |
| 7,794,503 B2 | 9/2010 | Daniels et al. |
| 7,799,029 B2 | 9/2010 | Jones |
| 7,828,851 B2 | 11/2010 | McCleary et al. |
| 7,833,275 B2 | 11/2010 | Mears et al. |
| 7,842,096 B2 | 11/2010 | Fridshtand et al. |
| 7,850,690 B2 | 12/2010 | Frigg et al. |
| 7,854,767 B2 | 12/2010 | May et al. |
| 7,901,411 B2 | 3/2011 | Frederick et al. |
| 7,909,881 B2 | 3/2011 | Boucher et al. |
| 7,914,584 B2 * | 3/2011 | Bigsby et al. ............. 623/22.42 |
| 7,947,135 B2 * | 5/2011 | Fonte ........................... 148/563 |
| 7,955,396 B2 * | 6/2011 | Terrill ....................... 623/22.44 |
| 7,998,217 B1 * | 8/2011 | Brown ..................... 623/20.15 |
| 7,998,218 B1 * | 8/2011 | Brown ..................... 623/20.35 |
| 8,029,573 B2 * | 10/2011 | Podolsky ................. 623/22.42 |
| 8,052,755 B2 * | 11/2011 | Naidu ....................... 623/21.12 |
| 8,062,378 B2 * | 11/2011 | Fonte ........................ 623/23.26 |
| 8,066,779 B2 | 11/2011 | Gibbs et al. |
| 8,095,198 B2 | 1/2012 | Nycz et al. |
| 8,114,166 B2 | 2/2012 | Auxepaules et al. |
| 8,133,284 B2 | 3/2012 | Ely et al. |
| 8,137,486 B2 * | 3/2012 | Fonte ............................ 148/563 |
| 8,152,669 B2 | 4/2012 | Maguire et al. |
| 8,152,814 B2 | 4/2012 | Jones et al. |
| 8,182,484 B2 | 5/2012 | Grant et al. |
| RE43,482 E | 6/2012 | Mikol et al. |
| 8,211,183 B2 * | 7/2012 | Podolsky .................. 623/22.15 |
| 8,257,835 B2 | 9/2012 | Jani et al. |
| 8,262,709 B1 | 9/2012 | Powlan |
| 8,282,646 B2 | 10/2012 | Schoenefeld et al. |
| 8,303,590 B2 | 11/2012 | Elghazaly et al. |
| 8,303,668 B2 * | 11/2012 | Despres et al. ............ 623/22.42 |
| 8,323,346 B2 | 12/2012 | Tepic |
| 8,323,349 B2 | 12/2012 | Schmid |
| 8,355,965 B2 | 1/2013 | Yamada |
| 8,357,205 B2 | 1/2013 | Rahaman et al. |
| 8,377,133 B2 | 2/2013 | Yuan et al. |
| 8,398,719 B2 | 3/2013 | Walter et al. |
| 8,398,790 B2 * | 3/2013 | Fonte ........................... 148/563 |
| 8,454,606 B2 | 6/2013 | Frigg et al. |
| 8,562,690 B1 * | 10/2013 | Dickerson ................. 623/22.42 |
| 8,579,985 B2 * | 11/2013 | Podolsky et al. .......... 623/22.42 |
| 2001/0008981 A1 * | 7/2001 | Masini ....................... 623/22.42 |
| 2001/0027345 A1 | 10/2001 | Merrill et al. |
| 2001/0049559 A1 | 12/2001 | Koo et al. |
| 2001/0049561 A1 * | 12/2001 | Dews et al. ............... 623/19.14 |
| 2001/0051831 A1 * | 12/2001 | Subba Rao et al. ....... 623/22.42 |
| 2002/0004685 A1 | 1/2002 | White |
| 2002/0007220 A1 | 1/2002 | Gie et al. |
| 2002/0038148 A1 * | 3/2002 | Fernandez et al. ........ 623/23.18 |
| 2002/0040244 A1 | 4/2002 | Despres et al. |
| 2002/0045900 A1 | 4/2002 | Harder et al. |
| 2002/0049500 A1 | 4/2002 | Draenert |
| 2002/0058999 A1 * | 5/2002 | Dwyer et al. .............. 623/22.42 |
| 2002/0072799 A1 | 6/2002 | Despres, III et al. |

(56) References Cited

U.S. PATENT DOCUMENTS

| | | | | |
|---|---|---|---|---|
| 2002/0072802 | A1 | 6/2002 | O'Neil et al. | |
| 2002/0103541 | A1 | 8/2002 | Meyers et al. | |
| 2002/0120340 | A1* | 8/2002 | Metzger et al. | 623/20.15 |
| 2002/0120343 | A1 | 8/2002 | Doubler et al. | |
| 2002/0133234 | A1 | 9/2002 | Sotereanos | |
| 2002/0143333 | A1 | 10/2002 | von Hoffmann et al. | |
| 2002/0151984 | A1 | 10/2002 | White | |
| 2002/0156473 | A1 | 10/2002 | Bramlet et al. | |
| 2002/0173792 | A1 | 11/2002 | Severns et al. | |
| 2003/0014119 | A1* | 1/2003 | Capon et al. | 623/19.11 |
| 2003/0014123 | A1* | 1/2003 | Copf et al. | 623/23.14 |
| 2003/0050704 | A1 | 3/2003 | Keynan | |
| 2003/0050706 | A1 | 3/2003 | Draenert et al. | |
| 2003/0071819 | A1 | 4/2003 | Kondo et al. | |
| 2003/0074000 | A1 | 4/2003 | Roth et al. | |
| 2003/0074079 | A1 | 4/2003 | McTighe et al. | |
| 2003/0074083 | A1* | 4/2003 | LeGros et al. | 623/23.35 |
| 2003/0088145 | A1* | 5/2003 | Scott | 600/8 |
| 2003/0125808 | A1 | 7/2003 | Hunter et al. | |
| 2003/0130741 | A1 | 7/2003 | McMinn | |
| 2003/0171819 | A1 | 9/2003 | Sotereanos | |
| 2003/0181987 | A1 | 9/2003 | Muirhead-Allwood | |
| 2003/0204268 | A1 | 10/2003 | Gerbec et al. | |
| 2004/0054419 | A1 | 3/2004 | Serra et al. | |
| 2004/0064188 | A1* | 4/2004 | Ball et al. | 623/19.11 |
| 2004/0068324 | A1* | 4/2004 | Grundei | 623/32 |
| 2004/0107594 | A1 | 6/2004 | Afriat | |
| 2004/0122525 | A1* | 6/2004 | Daniels et al. | 623/22.42 |
| 2004/0162621 | A1 | 8/2004 | Crofford | |
| 2004/0199259 | A1 | 10/2004 | Pichon et al. | |
| 2004/0210317 | A1* | 10/2004 | Maroney et al. | 623/19.14 |
| 2004/0220673 | A1* | 11/2004 | Pria | 623/19.12 |
| 2004/0260290 | A1 | 12/2004 | Zander et al. | |
| 2004/0267267 | A1 | 12/2004 | Daniels et al. | |
| 2004/0267372 | A1 | 12/2004 | Vanasse et al. | |
| 2004/0267373 | A1 | 12/2004 | Dwyer et al. | |
| 2005/0010223 | A1 | 1/2005 | Gotfried | |
| 2005/0010230 | A1 | 1/2005 | Crofford | |
| 2005/0015154 | A1 | 1/2005 | Lindsey et al. | |
| 2005/0049713 | A1* | 3/2005 | Garber et al. | 623/22.21 |
| 2005/0125067 | A1 | 6/2005 | Sweeney | |
| 2005/0149047 | A1 | 7/2005 | Parry et al. | |
| 2005/0177159 | A1 | 8/2005 | Guzman et al. | |
| 2005/0203536 | A1 | 9/2005 | Laffargue et al. | |
| 2005/0283254 | A1 | 12/2005 | Hayes et al. | |
| 2006/0004465 | A1 | 1/2006 | Bergin et al. | |
| 2006/0030947 | A1 | 2/2006 | Mears et al. | |
| 2006/0052877 | A9 | 3/2006 | Doubler et al. | |
| 2006/0106463 | A1* | 5/2006 | Bigsby et al. | 623/23.42 |
| 2006/0149247 | A1 | 7/2006 | Frigg et al. | |
| 2006/0155281 | A1 | 7/2006 | Kaup et al. | |
| 2006/0161262 | A1 | 7/2006 | Chen et al. | |
| 2006/0167557 | A1* | 7/2006 | Terrill | 623/22.43 |
| 2006/0173548 | A1 | 8/2006 | Auxepaules et al. | |
| 2006/0173549 | A1* | 8/2006 | Ragbir | 623/22.41 |
| 2006/0224245 | A1* | 10/2006 | Siebel | 623/22.11 |
| 2006/0241606 | A1 | 10/2006 | Vachtenberg et al. | |
| 2007/0038306 | A1 | 2/2007 | O'Gara | |
| 2007/0043446 | A1* | 2/2007 | Murray | 623/22.12 |
| 2007/0043448 | A1* | 2/2007 | Murray | 623/22.46 |
| 2007/0050041 | A1 | 3/2007 | Dietz et al. | |
| 2007/0055381 | A1* | 3/2007 | Berelsman et al. | 623/21.12 |
| 2007/0078464 | A1 | 4/2007 | Jones et al. | |
| 2007/0078519 | A1 | 4/2007 | Klotz | |
| 2007/0112430 | A1 | 5/2007 | Simmen et al. | |
| 2007/0142921 | A1* | 6/2007 | Lewis et al. | 623/22.36 |
| 2007/0173838 | A1* | 7/2007 | Li | 606/67 |
| 2007/0179568 | A1 | 8/2007 | Nycz et al. | |
| 2007/0179624 | A1* | 8/2007 | Stone et al. | 623/19.13 |
| 2007/0198094 | A1* | 8/2007 | Berelsman et al. | 623/19.14 |
| 2007/0219640 | A1 | 9/2007 | Steinberg | |
| 2007/0244566 | A1* | 10/2007 | Daniels et al. | 623/22.11 |
| 2007/0244567 | A1* | 10/2007 | Yang et al. | 623/23.46 |
| 2007/0255420 | A1 | 11/2007 | Johnson et al. | |
| 2007/0270846 | A1 | 11/2007 | Metzinger | |
| 2007/0270847 | A1 | 11/2007 | Shaw | |
| 2008/0051790 | A1 | 2/2008 | Defossez | |
| 2008/0133023 | A1* | 6/2008 | Schlotterback et al. | 623/22.42 |
| 2008/0140077 | A1 | 6/2008 | Kebaish | |
| 2008/0140210 | A1 | 6/2008 | Doubler et al. | |
| 2008/0147066 | A1 | 6/2008 | Longsworth et al. | |
| 2008/0243264 | A1* | 10/2008 | Fonte | 623/22.43 |
| 2008/0262498 | A1 | 10/2008 | Fernandez Dell'Oca | |
| 2008/0262629 | A1* | 10/2008 | Fonte | 623/23.15 |
| 2009/0005876 | A1* | 1/2009 | Dietz et al. | 623/20.36 |
| 2009/0076619 | A1 | 3/2009 | Grappiolo et al. | |
| 2009/0088862 | A1* | 4/2009 | Thomas et al. | 623/20.36 |
| 2009/0088863 | A1* | 4/2009 | Boucher et al. | 623/22.4 |
| 2009/0093887 | A1 | 4/2009 | Walter et al. | |
| 2009/0112330 | A1 | 4/2009 | Grundei | |
| 2009/0118837 | A1* | 5/2009 | Winslow et al. | 623/19.14 |
| 2009/0125028 | A1 | 5/2009 | Teisen et al. | |
| 2009/0149963 | A1* | 6/2009 | Sekel | 623/20.15 |
| 2009/0171466 | A1* | 7/2009 | Frazee et al. | 623/23.43 |
| 2009/0187255 | A1 | 7/2009 | Jani et al. | |
| 2009/0204226 | A1* | 8/2009 | Fonte | 623/23.15 |
| 2009/0264885 | A1 | 10/2009 | Grant et al. | |
| 2009/0270996 | A1* | 10/2009 | Meulink et al. | 623/22.42 |
| 2009/0281630 | A1* | 11/2009 | Delince et al. | 623/19.13 |
| 2009/0287214 | A1 | 11/2009 | Yu | |
| 2009/0306787 | A1* | 12/2009 | Crabtree et al. | 623/20.34 |
| 2009/0326534 | A1 | 12/2009 | Yamazaki et al. | |
| 2010/0063504 | A1 | 3/2010 | Munro et al. | |
| 2010/0094293 | A1 | 4/2010 | McClellan et al. | |
| 2010/0100193 | A1* | 4/2010 | White | 623/22.43 |
| 2010/0114324 | A1 | 5/2010 | Gibbs | |
| 2010/0137863 | A1 | 6/2010 | Munro | |
| 2010/0161069 | A1* | 6/2010 | Ragbir | 623/22.11 |
| 2010/0174284 | A1 | 7/2010 | Schwammberger et al. | |
| 2010/0174377 | A1 | 7/2010 | Heuer | |
| 2010/0174380 | A1 | 7/2010 | Lewis | |
| 2010/0179551 | A1 | 7/2010 | Keller et al. | |
| 2010/0179662 | A1 | 7/2010 | Verne et al. | |
| 2010/0191344 | A1 | 7/2010 | Grundei et al. | |
| 2010/0217265 | A1 | 8/2010 | Chen et al. | |
| 2010/0222891 | A1* | 9/2010 | Goodfried et al. | 623/20.36 |
| 2010/0228354 | A1 | 9/2010 | Ely et al. | |
| 2010/0241239 | A1 | 9/2010 | Smith | |
| 2010/0249781 | A1 | 9/2010 | Haidukewych et al. | |
| 2010/0249852 | A1 | 9/2010 | Brumfield et al. | |
| 2010/0249943 | A1* | 9/2010 | Bergin et al. | 623/22.42 |
| 2010/0256638 | A1 | 10/2010 | Tyber et al. | |
| 2010/0256758 | A1 | 10/2010 | Gordon et al. | |
| 2010/0268229 | A1 | 10/2010 | Siravo et al. | |
| 2011/0009965 | A1 | 1/2011 | Ankem | |
| 2011/0009976 | A1* | 1/2011 | Cruchet | 623/22.46 |
| 2011/0015752 | A1 | 1/2011 | Meridew | |
| 2011/0035021 | A1 | 2/2011 | Bergin et al. | |
| 2011/0046745 | A1 | 2/2011 | Daniels et al. | |
| 2011/0054474 | A1 | 3/2011 | Metzinger et al. | |
| 2011/0054626 | A1* | 3/2011 | Thomas et al. | 623/20.36 |
| 2011/0060337 | A1 | 3/2011 | Ferrante et al. | |
| 2011/0066253 | A1 | 3/2011 | Langhorn et al. | |
| 2011/0087228 | A1 | 4/2011 | Ferrante et al. | |
| 2011/0106270 | A1 | 5/2011 | Huff et al. | |
| 2011/0166665 | A1 | 7/2011 | Podolsky | |
| 2011/0192563 | A1 | 8/2011 | Fonte | 164/76.1 |
| 2011/0196369 | A1 | 8/2011 | Osman | |
| 2011/0196372 | A1 | 8/2011 | Murase | |
| 2011/0218641 | A1 | 9/2011 | Smith et al. | |
| 2011/0257758 | A1 | 10/2011 | Smith et al. | |
| 2011/0264233 | A1 | 10/2011 | Song | |
| 2011/0282395 | A1 | 11/2011 | Beyar et al. | |
| 2012/0010720 | A1 | 1/2012 | Dickerson | |
| 2012/0022661 | A1 | 1/2012 | McLean | |
| 2012/0065737 | A1* | 3/2012 | Chow | 623/22.42 |
| 2012/0123554 | A1* | 5/2012 | Fonte | 623/23.35 |
| 2012/0130502 | A1* | 5/2012 | Podolsky et al. | 623/22.4 |
| 2012/0157997 | A1 | 6/2012 | Sohngen | |
| 2012/0172992 | A1 | 7/2012 | Fockens | |
| 2012/0191092 | A1* | 7/2012 | Buettler et al. | 606/64 |
| 2012/0226283 | A1 | 9/2012 | Meridew et al. | |
| 2012/0226361 | A1 | 9/2012 | Podolsky | |
| 2013/0030543 | A1 | 1/2013 | Morrey et al. | |

(56) References Cited

U.S. PATENT DOCUMENTS

| | | | |
|---|---|---|---|
| 2013/0060347 A1 | 3/2013 | McMinn | |
| 2013/0073050 A1 | 3/2013 | McEntire et al. | |
| 2013/0079888 A1* | 3/2013 | Meulink | 623/22.42 |
| 2013/0204390 A1* | 8/2013 | Podolsky | 623/22.42 |
| 2013/0261762 A1* | 10/2013 | Kennedy | 623/22.42 |
| 2013/0310947 A1* | 11/2013 | Cremascoli et al. | 623/23.35 |
| 2014/0074250 A1* | 3/2014 | Podolsky et al. | 623/22.42 |
| 2014/0128986 A1* | 5/2014 | Podolsky | 623/22.4 |

FOREIGN PATENT DOCUMENTS

| | | |
|---|---|---|
| DE | 2854334 | 6/1980 |
| DE | 3205577 | 10/1982 |
| DE | 3340767 | 5/1985 |
| DE | 87 01 164 UI | 6/1987 |
| DE | 4031520 | 4/1992 |
| DE | 19505609 | 8/1996 |
| DE | 19610741 | 11/1997 |
| DE | 19723339 | 5/1999 |
| DE | 19852945 | 5/2000 |
| DE | 20007950 | 8/2000 |
| DE | 10120331 | 11/2002 |
| DE | 10223474 | 12/2003 |
| DE | 102005005657 | 8/2006 |
| EP | 0000549 | 2/1978 |
| EP | 0010527 | 4/1980 |
| EP | 0023608 | 2/1981 |
| EP | 0024008 | 2/1981 |
| EP | 0071242 | 2/1983 |
| EP | 0099167 | 1/1984 |
| EP | 0201407 | 11/1986 |
| EP | 0251583 | 1/1988 |
| EP | 0257118 | 3/1988 |
| EP | 0257359 | 3/1988 |
| EP | 0283706 | 9/1988 |
| EP | 0321170 | 6/1989 |
| EP | 0338774 | 10/1989 |
| EP | 0359457 | 3/1990 |
| EP | 0376658 | 7/1990 |
| EP | 0382395 | 8/1990 |
| EP | 0399920 | 11/1990 |
| EP | 0433121 | 6/1991 |
| EP | 0441577 | 8/1991 |
| EP | 0464961 | 1/1992 |
| EP | 0495340 | 7/1992 |
| EP | 0556997 | 8/1993 |
| EP | 0567349 | 10/1993 |
| EP | 0586824 | 3/1994 |
| EP | 0714645 | 6/1996 |
| EP | 0832620 | 4/1998 |
| EP | 0878177 | 11/1998 |
| EP | 0913132 | 5/1999 |
| EP | 1004283 | 5/2000 |
| EP | 1132064 | 9/2001 |
| EP | 1240879 | 9/2002 |
| EP | 1344505 | 9/2003 |
| FR | 1099519 | 9/1955 |
| FR | 1122634 | 9/1956 |
| FR | 2183230 | 12/1973 |
| FR | 2225141 | 11/1974 |
| FR | 2575383 | 7/1986 |
| FR | 2629707 | 10/1989 |
| FR | 2639820 | 6/1990 |
| FR | 2646078 | 10/1990 |
| FR | 2647669 A1 | 12/1990 |
| FR | 2651118 | 3/1991 |
| FR | 2674119 | 9/1992 |
| FR | 2705558 | 12/1994 |
| GB | 2209947 | 6/1989 |
| RU | 2108071 C1 | 4/1998 |
| RU | 2108766 C1 | 4/1998 |
| WO | WO 8505027 | 11/1985 |
| WO | WO 9308770 | 5/1993 |
| WO | WO 9417757 | 8/1994 |
| WO | WO 9613233 | 5/1996 |
| WO | WO 0072785 | 12/2000 |
| WO | WO 0149218 | 7/2001 |
| WO | WO 03094763 | 11/2003 |

OTHER PUBLICATIONS

International Search Report dated Aug. 10, 2012 for Application No. PCT/US2012/24161.

International Search Report; mailed Sep. 12, 2007; International Patent Application No. PCT/US2006/046795; 1 page.

Prokhorov, "Sovetskaya entisklopediya," Bolshaya sovetskaya entsiklopediya, Moscow, 1972, tom 8, p. 455-456, col. 1354, paragraph 1.

* cited by examiner

METHOD AND APPARATUS FOR ATTACHMENT IN A MODULAR HIP REPLACEMENT OR FRACTURE FIXATION DEVICE

CROSS-REFERENCE TO RELATED APPLICATIONS

This application claims the benefit of priority from U.S. Provisional Application No. 61/722,960 filed on Nov. 6, 2012 and is a continuation-in-part of U.S. application Ser. No. 13/335,216, filed on Dec. 22, 2011, which is a continuation-in-part of U.S. application Ser. No. 13/049,619, filed Mar. 16, 2011 and issued as U.S. Pat. No. 8,211,183, which is a divisional application of U.S. application Ser. No. 12/518,081, filed Jun. 5, 2009 and issued as U.S. Pat. No. 8,029,573, which is a U.S. National Phase application of PCT/US2006/046795, filed in English on Dec. 7, 2006 and published as WO 2008/069800 A1 on Jun. 12, 2008, each of which is incorporated by reference in its entirety herein. Any and all priority claims identified in the Application Data Sheet, or any correction thereto, are hereby incorporated by reference under 37 CFR 1.57.

BACKGROUND

1. Field

Embodiments of the present invention relate to medical methods and apparatus, and more particularly to a method and apparatus for attaching components in implants. In one embodiment, the components in an implant are attached in a manner to reduce fretting, debris, and/or material from wearing off the implant components. In one embodiment, a device includes a connection mechanism with a bore and cone interface. In one embodiment, a device includes a connection mechanism with a taper. In one embodiment, a device includes a connection mechanism with a thread. In one embodiment, a device includes a connection mechanism with a temperature differential. In various embodiments, any combination of features can used for a connection mechanism. In one embodiment, a device includes a connection mechanism between a prosthetic femoral neck implant to a prosthetic femoral head and/or prosthetic femoral stem implant in a total- or hemi-hip arthroplasty, and hip fracture fixation devices.

2. Description of the Related Art

In certain instances, failure of conventional implants can be attributed to wear between components in the implant. For example, metal on metal fretting and wear can result in debris or corrosion being released from the implant. In certain instances, failure of conventional artificial hip implants can be attributed to wear between a modular femoral neck implant with a femoral head implant. In certain instances, failure of conventional artificial hip implants can be attributed to wear between a modular femoral neck implant with a femoral stem or intramedullary rod implant. In some circumstances, metal on metal fretting and corrosion can lead to further damage. For example, in some conventional hip implants, fretting and/or crevice corrosion at the modular component junctions may occur. As loading is applied to the implant components from activities such as bearing weight, walking, and applying force at angles, relative micro-motion between the components can result in fretting, or wear of materials at pressure points at or near pivot points between the components. Conventional means of attaching a modular prosthetic neck can include tapping or hammering along the axis of a tapered connection, such as a Morse taper. Generally, conventional means of attaching components, such as the neck and stem or neck and head are difficult to align consistently and difficult to assemble using repeatable force. In some instances, conventional hip implants fail when the interface between the tapered surfaces are improperly aligned or seated, allowing rubbing, fretting, and wear resulting in the release of debris from the interface, which can result in increased blood serum metal levels, tissue inflammation, infection, pain, and/or necrosis. In some instances, these conventional designs can result in catastrophic failure. There is a need for an improved method and device for attaching components in implants. There is a need for an improved method and device for connections in implants that align the components and are able to apply controllable, reproducible force to engage the component connections. There is also a need for an improved method and device for attaching hip implants that use tapered connections, such as a femoral neck and/or stem and/or head, to other components in modular hip replacements.

SUMMARY

In accordance with some embodiments disclosed herein, various systems, components, and methods of use and surgery are provided to enhance the quality, reliability, and compatibility of implantation systems. These apparatuses and methods can be utilized for various types of implantation systems and methods of surgery, site and system preparation, and implantation. For example, embodiments of apparatuses disclosed herein for joint replacement may be used in joints of the human body. Embodiments of the methods disclosed herein can also be used for implanting medical devices in the body, such as prosthetic joints. These joints can include, but are not limited to the shoulder, the hip, the knee, etc. However, some embodiments can be provided in which the apparatuses and methods are used in other areas and with other structures. In some embodiments, implants are described in relation to a total hip arthroplasty. In some embodiments, implants are described in relation to a hemiarthroplasty, which includes a head replacement but no acetabular cup replacement.

In some embodiments, the present invention offers a total or partial hip replacement system and a hip fracture treatment device in combination with truly minimally invasive surgical (MIS) technique. In some embodiments, both femoral neck and intertrochanteric hip fractures can be treated. In some embodiments, hemiarthroplasty can be performed with a femoral neck and intramedullary rod for intertrochanteric fracture fixation.

In one embodiment, an implant includes components that can be modularly attached to each other. In one embodiment, implant components can be attached with an taper interface. In various embodiments, the taper can be a Morse taper, or comprise a bore and cone and/or one or more sloped surfaces in the interface. In one embodiment, a modular prosthetic femoral neck has a head engaging portion that comprises a taper and a thread for engagement of a modular prosthetic femoral head to the prosthetic femoral neck implant. In one embodiment, the implant component interface can include a thread. In one embodiment, the implant component interface can include a locking thread. In one embodiment, the system includes a combination of propelling threads and locking Morse taper surfaces on an axis parallel to, or same as, the longitudinal axis of a modular prosthetic femoral neck. In one embodiment, the thread is configured to lock the femoral neck implant component in the femoral head implant with an interference fit between the thread and the at least one tapered surface. In one embodiment, the distal neck portion includes the head engaging end, and/or a head engaging portion. In one embodiment, the head engaging portion includes a Morse taper and a thread. In one embodiment, the thread redistributes the loading and point of potential micro-motion between the neck and head, creating one, two, three, four, or more pivot points and localizing potential fretting to an isolated, threaded location at the interface. In one embodiment, fretting and materials released by micro-motion is sealed, trapped, or contained within an interface. In one embodiment, fretting and materials are contained within an interface by a taper, such as a Morse taper surface. In one embodiment, the combination of a thread with the taper surfaces provides three, four, or more point bending that can prevent or reduce micro-motion and reduce fretting and corrosion of the modular connection. In one embodiment, the interface has a two point bending connection. In one embodiment, the interface has a three point bending connection. In one embodiment, the interface has a four point bending connection. In one embodiment, the interface includes a trunnion taper lock. In one embodiment, a combination of propelling threads and locking Morse taper surfaces on the same (or parallel) axis of the modular femoral neck will resolve inaccuracies of manual impaction of the head onto the neck at the trunnion interface; resulting in consistent reduction of fretting and corrosion.

In one embodiment, a modular prosthetic femoral neck has a stem engaging portion that comprises a taper and a thread for engagement of a modular prosthetic femoral stem to the prosthetic femoral neck implant. In one embodiment, the system includes a combination of propelling threads and locking Morse taper surfaces on an axis parallel to, or same as, the longitudinal axis of a modular prosthetic femoral neck. In one embodiment, the thread is configured to lock the femoral neck implant component in the femoral stem implant with an interference fit between the thread and the at least one tapered surface. In one embodiment, the distal neck portion includes the stem engaging end, and/or a stem engaging portion. In one embodiment, the stem engaging portion includes a Morse taper and a thread. In one embodiment, the thread redistributes the loading and point of potential micro-motion between the neck and stem, creating one, two, three, four, or more pivot points and localizing potential fretting to an isolated, threaded location at the interface. In one embodiment, fretting and materials released by micro-motion is sealed, trapped, or contained within an interface. In one embodiment, fretting and materials are contained within an interface by a taper, such as a Morse taper surface. In one embodiment, the combination of a thread with the taper surfaces provides three, four, or more point bending that can prevent or reduce micro-motion and reduce fretting and corrosion of the modular connection. In one embodiment, the interface has a three point bending connection. In one embodiment, the interface has a four point bending connection. In one embodiment, the interface includes a trunnion taper lock. In one embodiment, a combination of propelling threads and locking Morse taper surfaces on the same (or parallel) axis of the modular femoral neck will resolve inaccuracies of manual impaction of the stem onto the neck at the trunnion interface; resulting in consistent reduction of fretting and corrosion.

In one embodiment, a prosthetic femoral neck can be attached to both a prosthetic femoral head and a prosthetic femoral stem with both interfaces comprising at least a taper and a thread each.

In one embodiment, prosthetic femoral neck includes an interface for adjustable engagement with a driving tool. In one embodiment, the prosthetic femoral head implant is configured to fit rotatably within a prosthetic acetabular cup in the acetabulum. In one embodiment, prosthetic femoral head includes an interface for adjustable engagement with a driving tool.

In one embodiment, the method includes lowering the temperature of at least a portion of the femoral neck component, interconnecting the femoral neck component with a femoral head component and/or a femoral stem component, and permitting the temperature of the portion of the femoral neck component to rise such that an interference fit between the femoral neck component and the femoral head and/or stem component is increased. In one embodiment, the method includes lowering the temperature of at least a portion of a third component, interconnecting the portion of the third component with a portion of at least one of the femoral neck component and the femoral head or stem component in a second interference fit; and permitting the temperature of the portion of the third component to rise such that the interference fit between the third component and one of the femoral neck component and the femoral head or stem component is increased. In one embodiment, a method of interconnecting components of a prosthetic joint system includes lowering the temperature of at least a portion of a first component, interconnecting the first portion of the first component with a second component in an interference fit, and permitting the temperature of the portion of the first component to rise such that the interference fit between the first and second components is increased. In one embodiment, the method further includes lowering the temperature of at least a portion of a third component, interconnecting the portion of the third component with a portion of at least one of the first and second components in an interference fit, and permitting the temperature of the portion of the third component to rise such that the interference fit between the third component and one of the first and second components is increased. In one embodiment, the first component is a femoral neck component of a prosthetic hip system and the second component is a femoral head component. In one embodiment, the first component is a femoral neck component of a prosthetic hip system and the second component is a femoral stem component. In one embodiment, the first component and the second component are interconnected with at least one Morse taper.

In some embodiments, the present invention offers an additional advantage with a prosthetic femoral neck that is attachable to a femoral stem. In one embodiment, a prosthetic femoral head is fixedly attached to the femoral neck. In one embodiment, a prosthetic femoral head is a monobody part of the femoral neck. In one embodiment, a prosthetic femoral head is modularly attachable to the femoral neck.

In some embodiments, the present invention offers an additional advantage with a prosthetic femoral neck that extends from a first point external to the femur and through the femur to a second point where it joins the prosthetic femoral head. In some embodiments, a modular neck component that is inserted laterally through a bore in the stem provides advantages in reducing the amount of rotation, dislocation, and tissue damage that occurs in other techniques. In one embodiment, a prosthetic femoral neck having a head engagement end is configured to fixedly join the neck engagement portion of the prosthetic femoral head, the prosthetic femoral neck configured to be advanced from a position along a side of a patient's body, through a side of the femur opposite the acetabulum, and through a lateral bore of the intramedullary rod such that the head engagement end of the prosthetic femoral neck fixedly joins the neck engagement portion of the prosthetic femoral head while a portion of the prosthetic femoral neck occupies the lateral bore. In various embodiments, the prosthetic femoral neck can be rotated to actuate and/or connect to the prosthetic femoral head.

Some embodiments of the present invention concern methods of performing a hip arthroplasty that can comprise some, or all of (1) surgically accessing an acetabulum, (2) preparing the acetabulum to receive a prosthetic acetabular cup (in embodiments with total hip arthroplasty), (3) seating the prosthetic acetabular cup in the prepared acetabulum, (4) fitting a prosthetic femoral head within the prosthetic acetabular cup (in embodiments with total hip arthroplasty), the prosthetic femoral head rotatable with respect to the prosthetic acetabular cup, (5) inserting a head-engaging end of a prosthetic femoral neck to engage the prosthetic femoral head, and (6) joining the head-engaging end of the prosthetic femoral neck to the prosthetic femoral head in any of the systems and methods disclosed herein. One embodiment further includes fixing the prosthetic femoral neck with respect to the prosthetic femoral head with a taper, such a Morse taper. One embodiment further includes fixing the prosthetic femoral neck with respect to the prosthetic femoral head with a thread. One embodiment further includes fixing the prosthetic femoral neck with respect to the prosthetic femoral head using a temperature differential.

Some embodiments of the present invention concern methods of performing a hip arthroplasty that can comprise some, or all of (1) surgically accessing an acetabulum, (2) preparing the acetabulum to receive a prosthetic acetabular cup (in embodiments with total hip arthroplasty), (3) seating the prosthetic acetabular cup in the prepared acetabulum, (4) fitting a prosthetic femoral head within the prosthetic acetabular cup, the prosthetic femoral head rotatable with respect to the prosthetic acetabular cup, (5) inserting a stem-engaging end of a prosthetic femoral neck to engage the prosthetic femoral stem, and (6) joining the stem-engaging end of the prosthetic femoral neck to the prosthetic femoral stem in any of the systems and methods disclosed herein. One embodiment further includes fixing the prosthetic femoral neck with respect to the prosthetic femoral stem with a taper, such a Morse taper. One embodiment further includes fixing the prosthetic femoral neck with respect to the prosthetic femoral stem with a thread. One embodiment further includes fixing the prosthetic femoral neck with respect to the prosthetic femoral stem using a temperature differential.

Some methods may also derive advantages from an embodiment wherein an alignment tool comprises a first fixation keyway and the femoral neck comprises a second fixation keyway which removably interlocks with the first fixation keyway to facilitate removable fixation of the alignment tool to the neck and/or head. The method may derive additional advantage from an embodiment wherein the diameters of the prosthetic acetabular cup and the prosthetic femoral head both exceed 50 millimeters.

In some embodiments, a prosthetic joint system and methods of use can be provided that utilizes a unique interconnection between joint components to provide a stable coupling with superior strength and permanence. For example, in an embodiment of a hip prosthesis system, a prosthetic femoral neck can be coupled to a prosthetic femoral head and/or stem using one or more Morse tapers. In one embodiment, portions of the neck and head are threadably coupled to each other. Further, in some embodiments, one or more components of the system can be cooled and thereby shrunk prior to being interconnected such that the components are able to warm and expand upon implantation and interconnection. In some embodiments, the components of the system, such as the prosthetic femoral neck, can be frozen in liquid nitrogen prior to interconnection with the support sleeve. Accordingly, in some embodiments, the Morse tapers of the components can achieve a high degree of interference without requiring forcible insertion and trauma.

These and other embodiments of the present invention are disclosed and described below. It will be appreciated that other embodiments and all substantial equivalents are within the scope of the inventions.

BRIEF DESCRIPTION OF THE DRAWINGS

Various features of embodiments of the inventions are described below with reference to the drawings. The illustrated embodiments are intended to illustrate, but not to limit, the inventions. The drawings described herein are for illustration purposes only and are not intended to limit the scope of the present disclosure in any way. Embodiments of the present invention will become more fully understood from the detailed description and the accompanying drawings. The drawings contain the following figures.

Throughout the figures, the same reference numerals and characters, unless otherwise stated, are used to denote like features, elements, components or portions of the illustrated embodiments. In certain instances, similar names may be used to describe similar components with different reference numerals which have certain common or similar features. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENT

While the present description sets forth specific details of various embodiments, it will be appreciated that the description is illustrative only and should not be construed in any way as limiting. Additionally, it is contemplated that although particular embodiments of the present inventions may be disclosed or shown in the context of hip surgeries, such as total hip arthroplasty or hemiarthroplasty, such embodiments can be used in other surgical techniques and devices. Furthermore, various applications of such embodiments and modifications thereto, which may occur to those who are skilled in the art, are also encompassed by the general concepts described herein.

Embodiments of the methods, systems, components, and devices disclosed herein can be used for various joints of the body, such as the shoulder, hip, and the like. As discussed in the above-noted publications, joint replacements for the hip are common and have several factors that can be considered when designing a hip prosthetic system and methods of implantation. In the present disclosure, reference is made to a prosthetic hip joint and system. However, the systems and methods disclosed herein can be used for various joints in the body. Thus, the present disclosure should be construed as applicable to methods, systems, components, and devices for any of the various joints of the body, such as the shoulder, hip, and the like.

In various embodiments, implants can include attachable components with interfaces. In one embodiment, a taper is included in an interface between implant components. In one embodiment, a taper comprises tapered surfaces, such as with a bore and a cone surface that complement each other. In one embodiment, the taper is a Morse taper. In one embodiment, a thread is included in an interface between implant components. In one embodiment, the thread is a locking thread. In one embodiment, a locking thread is configured to improve reliability of an interface connection under vibration. In one embodiment, a thread can lock the interface between tapered surfaces between implant components. In one embodiment, a thread can control the relative position and/or rotation of the bore and the cone to engage a taper via relative rotation. In one embodiment, a thread provides a controllable interface between tapered surfaces between implant components. In one embodiment, a thread can provide proper alignment between the bore and the cone to engage a tapered interface. In one embodiment, a thread can provide the ability to control a taper engagement force.

It will be appreciated that various surgical approaches may be used to access the femoral neck and acetabulum regions, and the present invention is not limited by any particular surgical approach. Nor is the present invention limited by any particular material for the prosthetic femoral head, prosthetic femoral neck, prosthetic femoral stem and/or an optional acetabular cup. Any of the components may be made from cobalt chromium, titanium, tantalum, surgical grade stainless steel, ceramic, alumina ceramic or other materials and/or alloys of suitable strength and acceptance properties.

Figure 1:
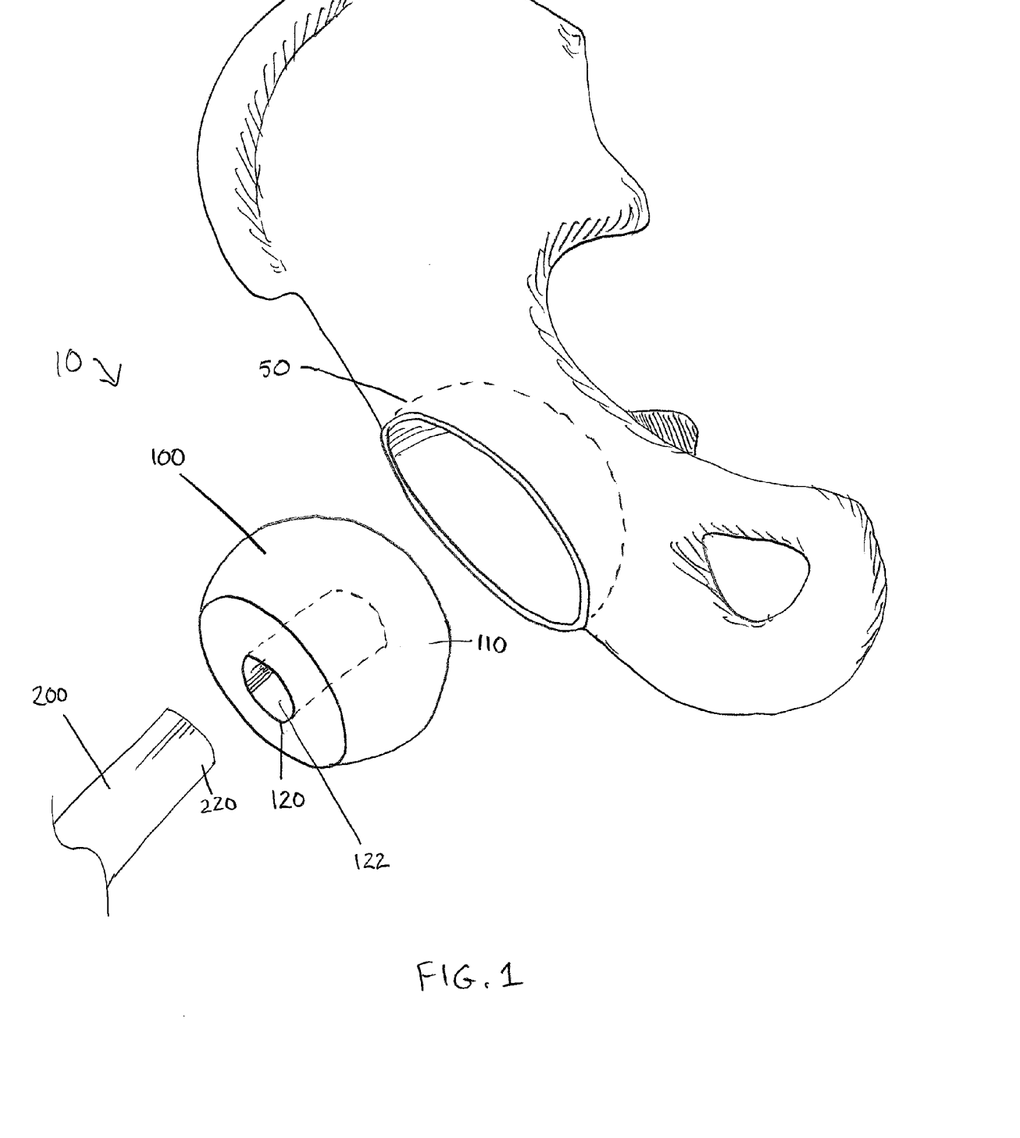
FIG. 1 illustrates an exploded view of a prosthetic hip system with a prosthetic femoral head, a prosthetic femoral neck and an optional prosthetic acetabular cup in accordance with one embodiment of the present invention.

In accordance with various embodiments, a prosthetic hip system 10 is provided for a minimally invasive, hip arthroplasty procedure. FIG. 1 illustrates an embodiment of a prosthetic hip system 10 with a prosthetic femoral head 100 positionable in an optional prosthetic acetabular cup 50. In one embodiment, a hemi-hip arthroplasty involves the attachment of a prosthetic femoral head 100 to a prosthetic femoral neck 200 implant. In one embodiment, a total hip arthroplasty further includes a prosthetic acetabular cup 50, which is seated in the acetabulum of the pelvis and is configured to allow rotational motion by the prosthetic femoral head 100. Although some figures may show a prosthetic acetabular cup 50, some embodiments of the present invention do not need to include a prosthetic acetabular cup 50.

In one embodiment, a prosthetic femoral head 100 is fit into a prosthetic acetabular cup 50. In one embodiment, the prosthetic femoral head 100 at a cup-engaging end 110 comprises a partial sphere having a curvature machined to precisely fit the inner surface of the prosthetic acetabular cup 50. The partial sphere of the prosthetic femoral head 100 may extend, in various embodiments from approximately 160 degrees to approximately 340 degrees, and thus may comprise any range from somewhat less than a hemisphere to nearly a full sphere. In one embodiment, the partial sphere of the prosthetic femoral head 100 is placed against the exposed rim of the hemispherical inner surface of the prosthetic acetabular cup 50. As will be appreciated, one or more light taps using a firm rubber-headed impacting tool may then seat the prosthetic femoral head properly into the prosthetic acetabular cup 50.

In one embodiment, the prosthetic femoral head 100 at a neck engaging end 120 includes structural means to receive and engage a prosthetic femoral neck 200. In a preferred embodiment, neck engagement may be achieved by a very slightly and narrowingly tapered cylindrical neck bore 122 machined approximately 2 cm into the prosthetic femoral head from the neck engaging end 120 inward toward the center of the prosthetic femoral head 100, such that a head-engaging end 220 of a prosthetic femoral neck 200 comprising roughly 2 cm of cylindrical shaft having a Morse taper matched to that of the neck bore 122 may be driven by impact into the neck bore 122, resulting in a fit sufficiently permanent to operatively support load-bearing movement about the prosthetic hip without slippage. In one embodiment, a neck bore 122 may extend more than or less than 2 cm into the prosthetic femoral head 100, and the head-engaging end 220 of the prosthetic femoral neck 200 will be of a roughly corresponding length of more than or less than 2 cm. Also, the diameter of the neck bore 122 will be approximately 11-13 mm (and will very gradually decrease as the bore extends into the prosthetic femoral head to accommodate the taper), although it will be appreciated that smaller or larger diameters may be used, and it will also be appreciated that the shaft diameter of the head-engaging end of the prosthetic femoral neck 200 will be of a diameter matching that of the neck bore 122.

In another embodiment (not shown), a different attachment technique may be used to join the prosthetic femoral head 100 to a prosthetic femoral neck 200. For example, the prosthetic femoral head 100, rather than include a neck bore 122, may include a neck shaft. The neck shaft may extend approximately 2 cm outward from the neck-engaging end 120 of the prosthetic femoral head 100. The neck shaft may be approximately 11-13 mm in diameter (though smaller or larger diameters could be used), with the diameter slightly decreasing along the neck shaft in the direction away from the center of the prosthetic femoral head, to form a Morse taper. It will be appreciated that a prosthetic femoral neck in approximately the form of a cylindrical shaft, may be machined to include a bore in one end having a receiving Morse taper of proper dimension to engage the neck shaft. It will be appreciated that still further methods and structures exist that could be adapted to the prosthetic femoral head and prosthetic femoral neck to facilitate the joining of these two prostheses.

In various embodiments, the neck bore 122 is any shaped interface. In one embodiment, the neck bore 122 is round. In one embodiment, the neck bore 122 is oval. The neck bore 122 is configured to receive the neck implant 200. The neck bore 122 can comprise one or more registration structures to rotationally secure the neck implant 200. The registration structures can comprise one or more protrusions and/or recesses extending along an outer surface of the neck implant 200 and/or the neck bore 122. In one embodiment, the neck bore 122 includes one or more threads or threaded portions. In one embodiment, the neck bore 122 includes one, two, or more tapered surfaces 124. In one embodiment, the tapered surface 124 is a Morse taper. In one embodiment, the distal bore end 5134 includes one, two, or more tapered surfaces 124. In one embodiment, the tapered surface 124 is a Morse taper. In various embodiments, the taper 124 is configured to seal the interface between system parts to prevent the escape of debris or flaking from components that may rub against each other in use. In various embodiments, the taper 124 is configured to provide an adjustable interface to account for differences in tolerances in dimensions between parts or components.

Figure 5:
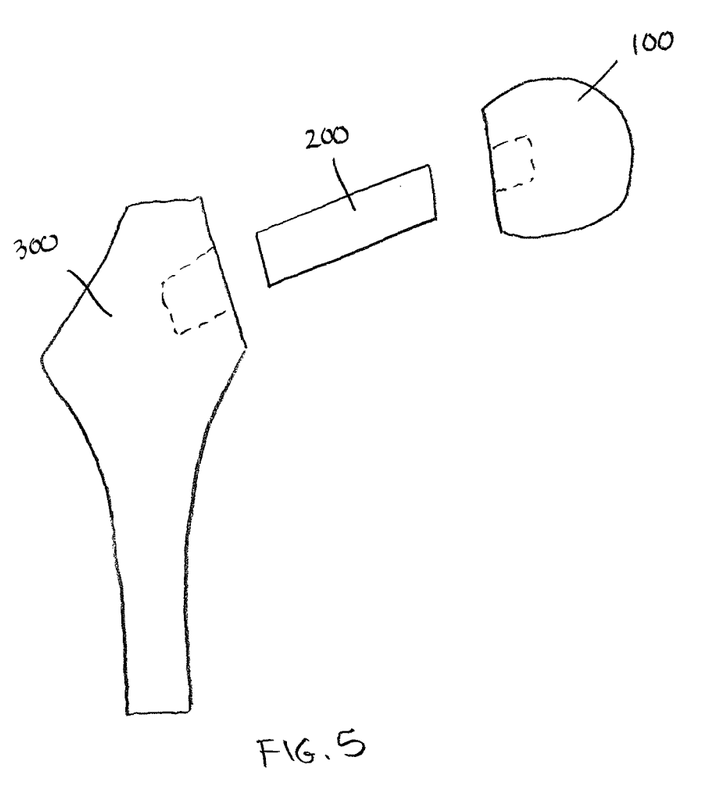
FIG. 5 illustrates an exploded view of a prosthetic hip system with a prosthetic femoral head, a prosthetic femoral neck and a prosthetic femoral stem in accordance with one embodiment of the present invention.

In accordance with various embodiments, a prosthetic hip system 10 is provided for a minimally invasive, hip arthroplasty procedure. FIG. 5 illustrates an embodiment of a prosthetic hip system 10 with a prosthetic femoral head 100, a prosthetic femoral neck 200 and a prosthetic femoral stem 300. In various embodiments, any of the prosthetic femoral neck 200 and either the prosthetic femoral head 100 or prosthetic femoral stem 300 can be permanently attached or constructed from a monolithic material. In some embodiments, only a prosthetic femoral head 100 can be attached to the prosthetic hip system 10, such as through a threaded interface in which the prosthetic femoral head 100 is rotated about a thread. In some embodiments, only a prosthetic femoral neck 200 can be attached to the prosthetic femoral stem 300, such as through a threaded interface in which the prosthetic femoral neck 200 is rotated about a thread.

In one embodiment, the prosthetic femoral stem 300 at a neck engaging end 320 includes structural means to receive and engage a prosthetic femoral neck 200. In a preferred embodiment, neck engagement may be achieved by a very slightly and narrowingly tapered cylindrical neck bore 322 machined approximately 2 cm into the prosthetic femoral head from the neck engaging end 320 inward toward the center of the prosthetic femoral stem 300, such that a stem-engaging end 225 of a prosthetic femoral neck 200 comprising roughly 2 cm of cylindrical shaft having a Morse taper matched to that of the neck bore 322 may be driven by impact into the neck bore 322, resulting in a fit sufficiently permanent to operatively support load-bearing movement about the prosthetic hip without slippage. In one embodiment, a neck bore 322 may extend more than or less than 2 cm into the prosthetic femoral stem 300, and the stem-engaging end 225 of the prosthetic femoral neck 200 will be of a roughly corresponding length of more than or less than 2 cm. Also, the diameter of the neck bore 322 will be approximately 11-13 mm (and will very gradually decrease as the bore extends into the prosthetic femoral stem to accommodate the taper), although it will be appreciated that smaller or larger diameters may be used, and it will also be appreciated that the shaft diameter of the stem-engaging end 225 of the prosthetic femoral neck 200 will be of a diameter matching that of the neck bore 322.

In some embodiments, a tapered surface 124, 224, 324 can be a Morse taper. In various embodiments, the taper 124, 224, 324 can be in the range of 0-10 degrees, 1-9 degrees, 2-8 degrees, 4-7 degrees, 5-6 degrees. In various embodiments, one, two or more tapers 124, 224, 324 can extend along between about 0.1-3, 0.5-2, 1-1.5 cm and/or less than or equal to about 3 cm of the distal neck portion 210 and/or a proximal neck portion of the femoral neck implant component 200. In various embodiments, one, two or more tapers 124, 224, 324 can extend along about 2 cm of a component. In various embodiments, the diameter of the bore can be between at least about 10 mm and/or less than or equal to about 17 mm. In some embodiments, the diameter of the bore can be between at least about 11 mm and/or less than or equal to about 15 mm. Further, the diameter of the distal section of the bore can be between at least about 10 mm and/or less than or equal to about 17 mm.

Figure 6:
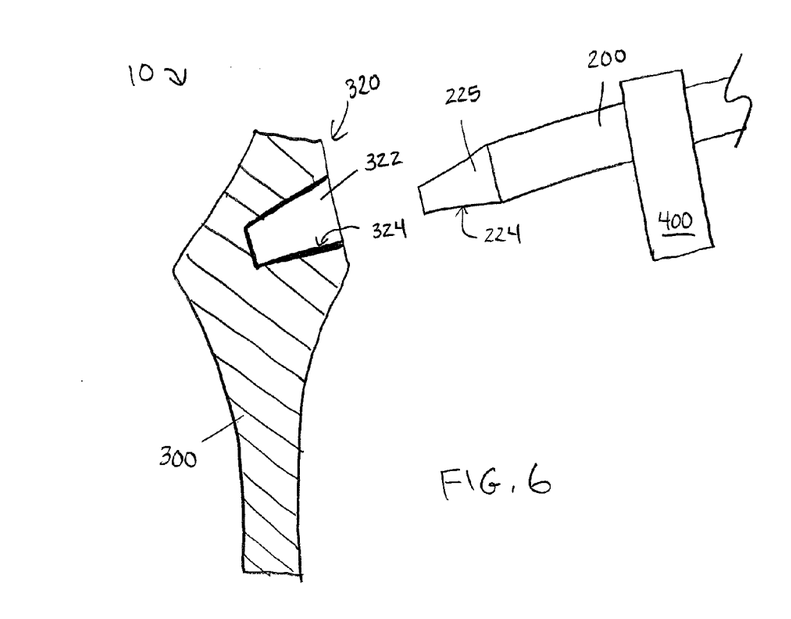
FIG. 6 illustrates a temperature differential applied to a prosthetic femoral neck for attachment to a prosthetic femoral stem in accordance with one embodiment of the present invention.

In one embodiment, a prosthetic femoral neck 200 may be a straight shaft, which may be slightly tapered on one end to fixedly join a prosthetic femoral head 100 by insertion into a neck bore 122 (see FIG. 1 and related description), and/or which may be slightly tapered on one end to fixedly join a prosthetic femoral stem 300 by insertion into a neck bore 322 (see FIGS. 5, 6 and related description). In one embodiment, a prosthetic femoral neck 200 may have a circular cross section. It will be appreciated that the cross-sectional shape may differ, and other embodiments are specifically contemplated such as, for example, oval, square, rectangular, triangular, irregular or other cross-sectional shapes may be used, where the shape of the neck bore 122 in the prosthetic femoral head 100 and/or the neck bore 322 in the prosthetic femoral stem 300 is configured to correspondingly receive a prosthetic femoral neck 200 having such cross-sectional shape. While a circular cross-section of a head-engaging end 220 of a prosthetic femoral neck may be used with the remainder of the prosthetic femoral neck 200 and/or a stem-engaging end 225 having a different cross-sectional shape, in another embodiment the neck-receiving bore 122 in the prosthetic femoral head 100 may be configured to receive a head-engaging end 220 of a prosthetic femoral neck 200 having a cross-sectional shape other than circular. In one embodiment, the neck-receiving bore 322 in the prosthetic femoral stem 300 may be configured to receive a stem-engaging end 225 of a prosthetic femoral neck 200 having a cross-sectional shape other than circular. In another embodiment, a prosthetic femoral neck 200 may be curved and/or may include fixation grooves. It will be appreciated that the prosthetic femoral neck 200 may be used to facilitate advantageous angling of the femoral head and/or femoral stem and also may be used for right or left hip joint repair simply by flipping it upside down.

In various embodiments of a prosthetic hip system 10, a prosthetic femoral neck 200 is attachable to another component, such as a prosthetic femoral head 100 and/or a prosthetic femoral stem 300, wherein the components are attached with one, two, or more interfaces, threads, locks, pins, locking screws, top locking screws, seals, adhesives, glues, cement, temperature differentials, cold welding, interference fits, tapers, Morse tapers, impacting, tapping, hammering, and/or other attachment mechanisms. In various embodiments, the prosthetic hip system 10 may have one, two, three, or more components, parts, portions, features, or sub-components that are attachable that include one, two, or more interfaces, threads, locks, pins, locking screws, top locking screws, seals, adhesives, glues, cement, temperature differentials, cold welding, interference fits, tapers, Morse tapers, impacting, tapping, hammering, and/or other attachment mechanisms. According to some embodiments, methods and systems for providing stable and secure interconnection of components are provided. Some embodiments can utilize structural interconnections that create press or interference fits between interlocking components. Some embodiments can utilize rotational or translational couplings that involve the use of torque or other force to engage the components. In various embodiments, any components can be joined or attached in any way—for example, the neck implant 200 connectable to a head implant 100 and/or a stem implant 300, or any components, parts, portions, features, or sub-components thereof.

Further, some embodiments can utilize joining techniques that can enhance the interconnection of the components, such as by the use of temperature differential through heating or cooling the components to enhance a press, taper and/or interference fit. In various embodiments, components can be manufactured from the same or different materials in order to achieve desired characteristics and temperature-dimensional responsiveness. In some embodiments, at least a portion of one or more of interconnecting components can be cooled, such as by a nitrogen bath, to cause interconnecting aspects of the component to be reduced in size or dimension prior to being coupled with the other component. For example, once cooled, the interconnection aspects can be coupled to achieve a maximum press or interference fit in a cooling stage. Thereafter, as the component warms and expands, the engagement provided by the press or interference fits can be enhanced as dimensions of the interconnecting aspects of the components increase, thereby enhancing the interference and contact between the interconnecting aspects of the components.

Figure 2:
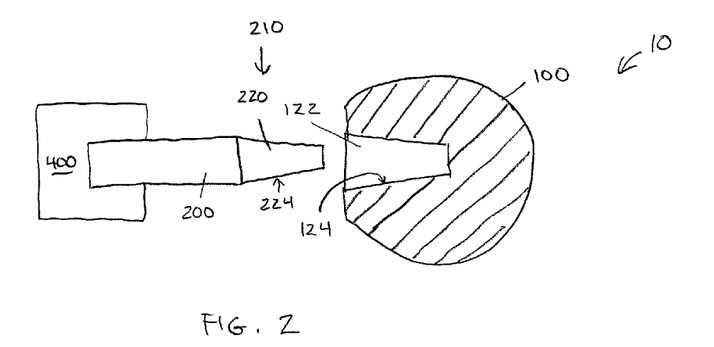
FIG. 2 illustrates a temperature differential applied to a prosthetic femoral neck for attachment to a prosthetic femoral head in accordance with one embodiment of the present invention.

As shown in FIGS. 2 and 6, in some embodiments, a temperature differential 400 can be applied to one or more components to expand or shrink a component material or part, such that upon equalization of temperature an interference fit, cold-weld, or other attachment holds or supplements the connection between the components. A living human body has a body temperature of roughly 37 degrees Celsius. Various compositions or materials are available in the operating room to cool components. For example, a ratio of 1:2.5 of $CaCl_2.6H_2O$/ice is roughly −10 degrees Celsius, a ratio of 1:3 of NaCl/ice is roughly −20 degrees Celsius, carbon tetrachloride/$CO_2$ is roughly −23 degrees Celsius, acetonitrile/$CO_2$ is roughly −42 degrees Celsius, a ratio of 1:0.8 $CaCl_2.6H_2O$/ice is roughly −40 degrees Celsius, Acetone/$CO_2$ is roughly −78 degrees Celsius, Methanol/$N_2$ is roughly −98 degrees Celsius, and liquid nitrogen (Liquid $N_2$) is roughly −196 degrees Celsius. In one embodiment, a freezer or refrigerating unit is used to cool a component.

In one embodiment, a temperature differential 400 includes cooling a component of the prosthetic hip system 10 and/or tooling associated with the prosthetic hip system 10. Once the cooled component is implanted in vivo, the body temperature of the patient warms the cooled component, resulting in some material expansion to improve a connection between components. In various embodiments, cooling through a temperature differential 400 can benefits that include less-traumatic hammering, less damage, automatically locking features, improved connection through a cold weld, reduction in component material flaking or debris, reduction in dispersal of flaking or debris, minimal damage to tissue, materials such as metals tend to equalize in temperature through thermal conduction before tissue is damaged. In one embodiment, cooling of one or more parts or components through a temperature differential 400 can cause condensation or the formation of moisture from the surrounding air, which can act as a lubricant to aid the insertion or implantation process.

In one embodiment, as shown in FIG. 2, the prosthetic femoral neck 200 implant is cooled and inserted in to a prosthetic femoral head 100. In one embodiment, as shown in FIG. 6, the prosthetic femoral neck 200 implant is cooled and inserted in to a prosthetic femoral stem 300. When the prosthetic femoral neck 200 implant warms, it expands and further locks the prosthetic femoral head 100 and/or stem 300 to the prosthetic femoral neck 200, such as in one embodiment, by engaging a taper. In one embodiment, the femoral neck implant 200 can be cooled prior to installation into the bore of the head implant 100 and/or stem implant 300 in order to create material shrinkage of the neck implant 200. In one embodiment, the size of the neck implant 200 can be reduced such that upon installation, the neck implant 200 can heat up and expand to create an interference fit with the bore of the neck engaging end 120 of the prosthetic femoral head 100 by virtue of the expanding size of the neck within the bore. In one embodiment, the size of the neck implant 200 can be reduced such that upon installation, the neck implant 200 can heat up and expand to create an interference fit with the bore of the neck engaging end 320 of the prosthetic femoral stem 300 by virtue of the expanding size of the neck within the bore. In various embodiments, additional parts or sub-components in the prosthetic hip system 10 can have temperature differentials 400 applied to improve the connection between parts or sub-components. Combinations of cooling with one, two or more tapers, threads, or other features are contemplated. Some embodiments can provide advantages that are superior to some traditional interfaces that may be driven together by impact or force in order to create in a fit sufficiently permanent to operatively support load-bearing movement about the prosthetic hip without slippage. Although such interface joining techniques can provide a tight fit, such structures and methods of use involve a high degree of force and can be undesirable for providing a careful, yet secure installation procedure. In contrast, embodiments disclosed herein provide exceptional engagement and fit. Further, some embodiments provide superior engagement using a unique cooling process to achieve maximum interference between mated surfaces and features of the components of the system.

Figure 3:
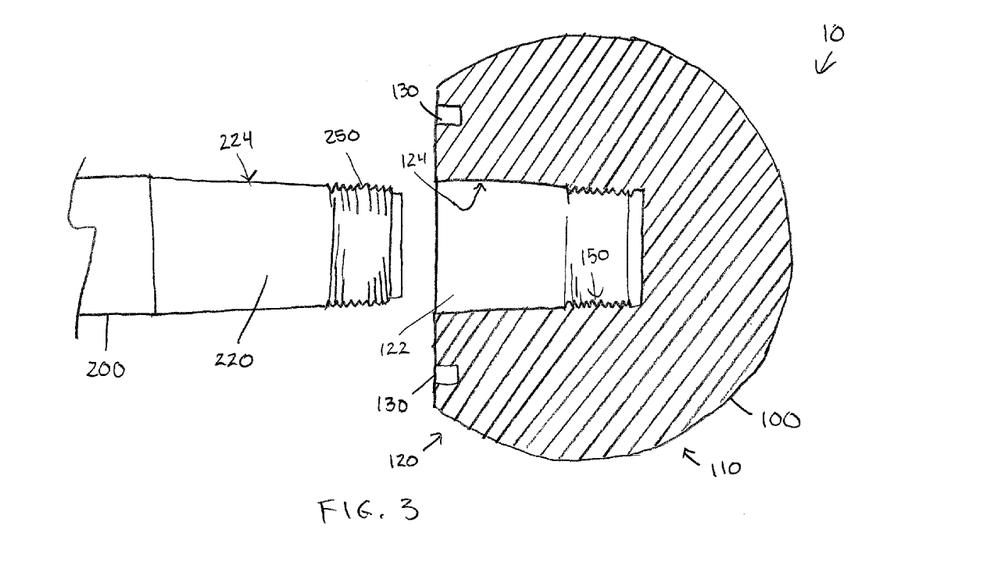
FIG. 3 illustrates a prosthetic femoral head attachable to a prosthetic femoral neck with a thread and a tapered surface interface in accordance with one embodiment of the present invention.

As shown in FIG. 3, in one embodiment, a prosthetic hip system 10 includes a neck implant 200 with a neck thread 250 that is connectable to a head implant 100 with a head thread 150. In one embodiment, the threads 150, 250 provide a tightenable, locking interface. In one embodiment, the threads 150, 250 are reversible for disassembly. In one embodiment, the threads 150, 250 operate in conjunction with a tapered surface to attach a neck implant 200 to a head implant 100. In one embodiment, the tapered surfaces 124, 224 are complementary Morse tapers. In one embodiment, a temperature differential 400 is applied to the threaded prosthetic hip system 10.

In one embodiment, the threaded prosthetic hip system 10 is assembled by inserting the prosthetic femoral neck 200 in to the prosthetic femoral head 100 and rotating the neck 200 and head 100 with respect to each other to engage the complementary threads 150, 250. As the threads 150, 250 bring the head 100 and neck 200 together, complementary tapered surfaces 124, 224 can engage each other. With the threaded interface, hammering is not necessary. With the threaded interface, a precise, repeatable attachment can performed with higher precision. In one embodiment, a tool can be configured to deliver a precise or maximum torque to tighten the threads.

In one embodiment, the threads 250, 150 are positioned at a distal end or near the distal end of the a prosthetic femoral neck 200 head engaging end 220 and the neck bore 122 in the prosthetic femoral head 100. One advantage of positioning threads at the distal end of the interface is that fretting or debris resulting from micro-motion of the interface localized to the threads will be trapped or contained within the distal end of the interface. In other embodiments, the threads 250, 150 can be positioned at any point, proximal, medial, distal, or otherwise along the prosthetic femoral neck 200 head engaging end 220 and the neck bore 122 in the prosthetic femoral head 100.

In one embodiment, a modular, threaded prosthetic hip system 10 includes a prosthetic femoral neck 2000 with a head engaging portion 220 that comprises a taper 224 and a thread 250 for attachable engagement to a modular prosthetic femoral head 100 to the prosthetic femoral neck 200 implant. In one embodiment, the system 10 includes a combination of propelling threads 150, 250 and locking Morse taper surfaces 124, 224 on an axis parallel to, or same as, the longitudinal axis of a modular prosthetic femoral neck 200. In one embodiment, the threads 150, 250 are configured to lock the femoral neck implant 200 component to the femoral head implant 100 with an interference fit between the threads 150, 250 and the at least one tapered surface 124, 224. In one embodiment, the distal neck portion includes the head engaging end, and/or a head engaging portion. In one embodiment, the head engaging portion includes a Morse taper and a thread. In one embodiment, the thread 150, 250 redistributes the loading and point of potential micro-motion between the neck 200 and head 100, creating one, two, three, four, or more pivot points and localizing potential fretting to an isolated, threaded location at the interface. In one embodiment, fretting and materials released by micro-motion are sealed, trapped, or contained within the interface. In one embodiment, fretting and materials are contained within an interface by a taper, such as a Morse taper surface. In one embodiment, the combination of a thread with the taper surfaces provides one, two, three, four, or more point bending that can prevent or reduce micro-motion and reduce fretting and corrosion of the modular connection. In one embodiment, the interface has a two point bending connection. In one embodiment, the interface has a three point bending connection. In one embodiment, the interface has a four point bending connection. In one embodiment, the interface includes a trunnion taper lock. In one embodiment, a combination of propelling threads and locking Morse taper surfaces on the same (or parallel) axis of the modular femoral neck will resolve inaccuracies of manual impaction of the head onto the neck at the trunnion interface; resulting in consistent reduction of fretting and corrosion.

Figure 4:
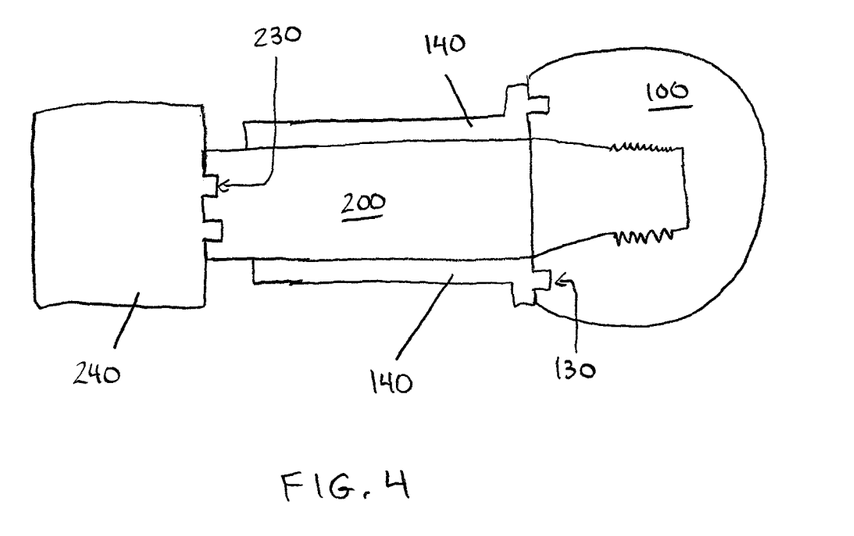
FIG. 4 illustrates a head tool for a prosthetic femoral head and a neck tool for a prosthetic femoral neck in accordance with one embodiment of the present invention.

As shown in FIG. 4, in one embodiment, the prosthetic femoral neck 200 includes a neck tool engaging portion 230 configured for a neck tool 240 for implantation, actuation, assembly, rotation, threading, and/or removing the prosthetic femoral neck 200. In various embodiments, the neck tool engaging portion 230 is a slot, keyed interface, hexagonal, or other interface for rotating the prosthetic femoral neck 200 to engage the neck thread 250 with the head thread 150. In one embodiment, the neck tool engaging portion 230 is on a proximal end of the prosthetic femoral neck 200, and the neck tool engaging portion 230 includes features for rotatable engagement. In various embodiments, the neck tool 230 can apply 0-5000, 0-4000, 0-500, 0-2000, 0-1000, 0-100, 10-80, 20-70, 30-60, 33, 45, and/or 55 ft-lb of torque to the neck thread 250.

In one embodiment, a head tool 140 includes one or more pins, keys, or other interface to hold the prosthetic femoral head 100 in position while a threaded prosthetic femoral neck 200 is threaded to the head 100. In one embodiment, no neck tool 240 is needed. In one embodiment, the prosthetic femoral neck 200 is in a fixed position, and the head tool 140 is configured to spin the prosthetic femoral head 100 to engage or disengage the threads. In various embodiments, the head tool 140 can apply 0-5000, 0-4000, 0-3000, 0-2000, 0-1000, 0-500, 0-100, 10-80, 20-70, 30-60, 33, 45, and/or 55 ft-lb of torque to the neck thread 250.

Figure 7:
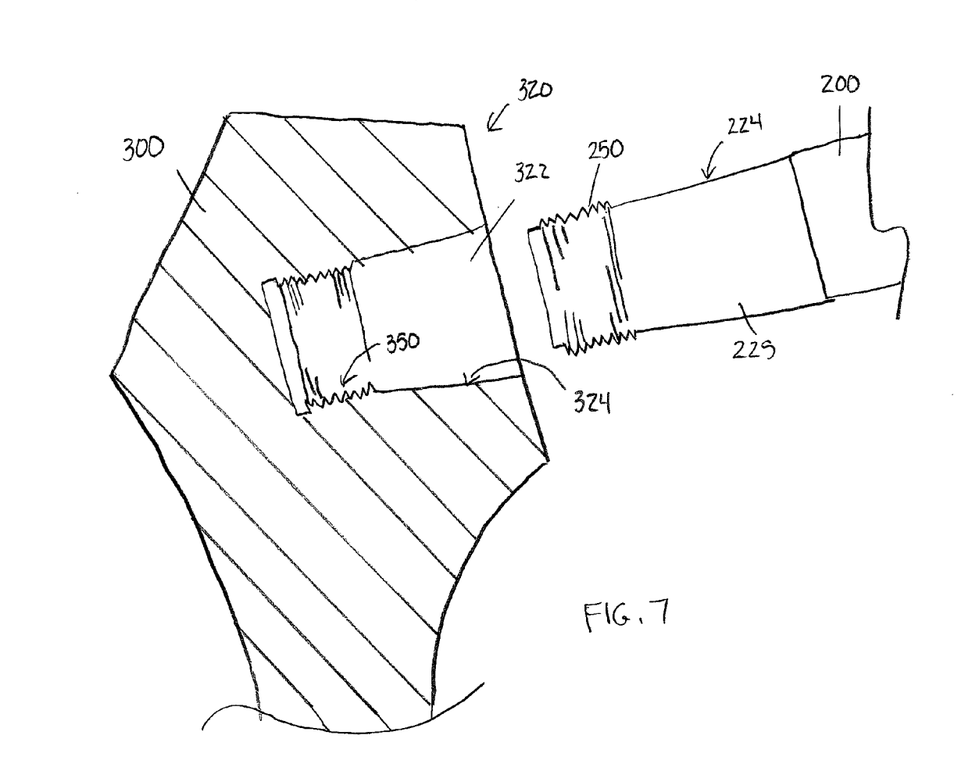
FIG. 7 illustrates a prosthetic femoral stem attachable to a prosthetic femoral neck with a thread and a tapered surface interface in accordance with one embodiment of the present invention.

As shown in FIG. 7, in one embodiment, a prosthetic hip system 10 includes a neck implant 200 with a neck thread 250 that is connectable to a stem implant 300 with a stem thread 350. In one embodiment, the threads 350, 250 provide a tightenable, locking interface. In one embodiment, the threads 350, 250 are reversible for disassembly. In one embodiment, the threads 350, 250 operate in conjunction with a tapered surface to attach a neck implant 200 to a stem implant 300. In one embodiment, the tapered surfaces 324, 224 are complementary Morse tapers. In one embodiment, a temperature differential 400 is applied to the threaded prosthetic hip system 10.

In one embodiment, the threaded prosthetic hip system 10 is assembled by inserting the prosthetic femoral neck 200 in to the prosthetic femoral stem 300 and rotating the neck 200 and stem 300 with respect to each other to engage the complementary threads 350, 250. As the threads 350, 250 bring the stem 300 and neck 200 together, complementary tapered surfaces 324, 224 can engage each other. With the threaded interface, hammering is not necessary. With the threaded interface, a precise, repeatable attachment can performed with higher precision. In one embodiment, a tool can be configured to deliver a precise or maximum torque to tighten the threads.

In one embodiment, the threads 250, 350 are positioned at a proximal end or near the proximal end of the a prosthetic femoral neck 200 stem engaging end 225 and the neck bore 322 in the prosthetic femoral stem 300. One advantage of positioning threads at the proximal, or "deep" end of the interface is that fretting or debris resulting from micro-motion of the interface localized to the threads will be trapped or contained within the interface. In other embodiments, the threads 250, 350 can be positioned at any point, proximal, medial, distal, or otherwise along the prosthetic femoral neck 200 stem engaging end 225 and the neck bore 322 in the prosthetic femoral stem 300.

In one embodiment, a modular, threaded prosthetic hip system 10 includes a prosthetic femoral neck 2000 with a stem engaging portion 225 that comprises a taper 224 and a thread 250 for attachable engagement to a modular prosthetic femoral stem 300 to the prosthetic femoral neck 200 implant. In one embodiment, the system 10 includes a combination of propelling threads 350, 250 and locking Morse taper surfaces 324, 224 on an axis parallel to, or same as, the longitudinal axis of a modular prosthetic femoral neck 200. In one embodiment, the threads 350, 250 are configured to lock the femoral neck implant 200 component to the femoral stem implant 300 with an interference fit between the threads 350, 250 and the at least one tapered surface 324, 224. In one embodiment, the proximal neck portion includes the stem engaging end, and/or a stem engaging portion. In one embodiment, the stem engaging portion includes a Morse taper and a thread. In one embodiment, the thread 350, 250 redistributes the loading and point of potential micro-motion between the neck 200 and stem 300, creating one, two, three, four, or more pivot points and localizing potential fretting to an isolated, threaded location at the interface. In one embodiment, fretting and materials released by micro-motion are sealed, trapped, or contained within the interface. In one embodiment, fretting and materials are contained within an interface by a taper, such as a Morse taper surface. In one embodiment, the combination of a thread with the taper surfaces provides one, two, three, four, or more point bending that can prevent or reduce micro-motion and reduce fretting and corrosion of the modular connection. In one embodiment, the interface has a two point bending connection. In one embodiment, the interface has a three point bending connection. In one embodiment, the interface has a four point bending connection. In one embodiment, the interface includes a trunnion taper lock. In one embodiment, a combination of propelling threads and locking Morse taper surfaces on the same (or parallel) axis of the modular femoral neck will resolve inaccuracies of manual impaction of the stem onto the neck at the trunnion interface; resulting in consistent reduction of fretting and corrosion.

Figure 8:
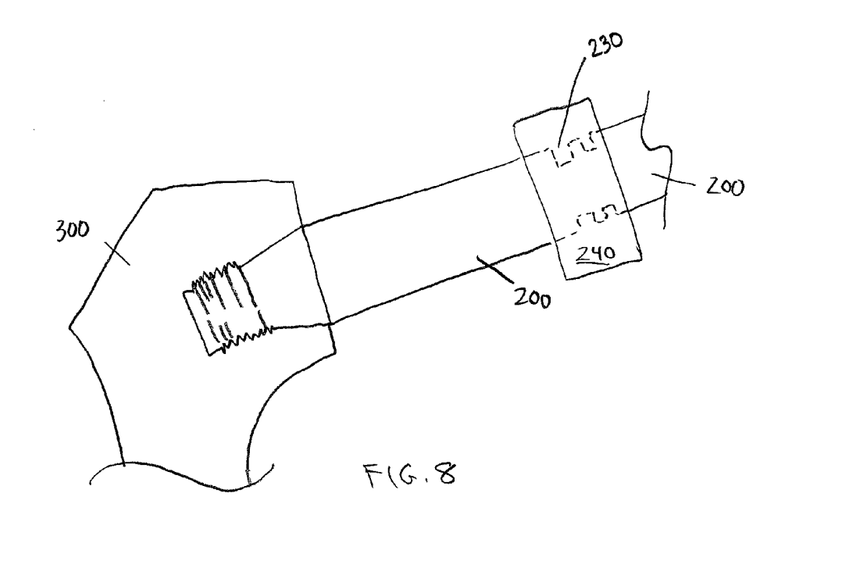
FIG. 8 illustrates a neck tool for a prosthetic femoral neck in accordance with one embodiment of the present invention.

As shown in FIG. 8, in one embodiment, the prosthetic femoral neck 200 includes a neck tool engaging portion 230 configured for a neck tool 240 for implantation, actuation, assembly, rotation, threading, and/or removing the prosthetic femoral neck 200. In various embodiments, the neck tool engaging portion 230 is a slot, keyed interface, hexagonal, or other interface for rotating the prosthetic femoral neck 200 to engage the neck thread 250 with the stem thread 350.

In various embodiments, the neck tool engaging portion 230 can be attached at any point along the prosthetic femoral neck 200, and the neck tool engaging portion 230 includes features for rotatable engagement. In various embodiments, the neck tool 230 can apply 0-5000, 0-4000, 0-3000, 0-2000, 0-1000, 0-500, 0-100, 10-80, 20-70, 30-60, 33, 45, and/or 55 ft-lb of torque to the neck thread 250.

In one embodiment, a stem tool 340 includes one or more pins, keys, or other interface to hold the prosthetic femoral stem 300 in position while a threaded prosthetic femoral neck 200 is threaded to the stem 300.

Figure 9:
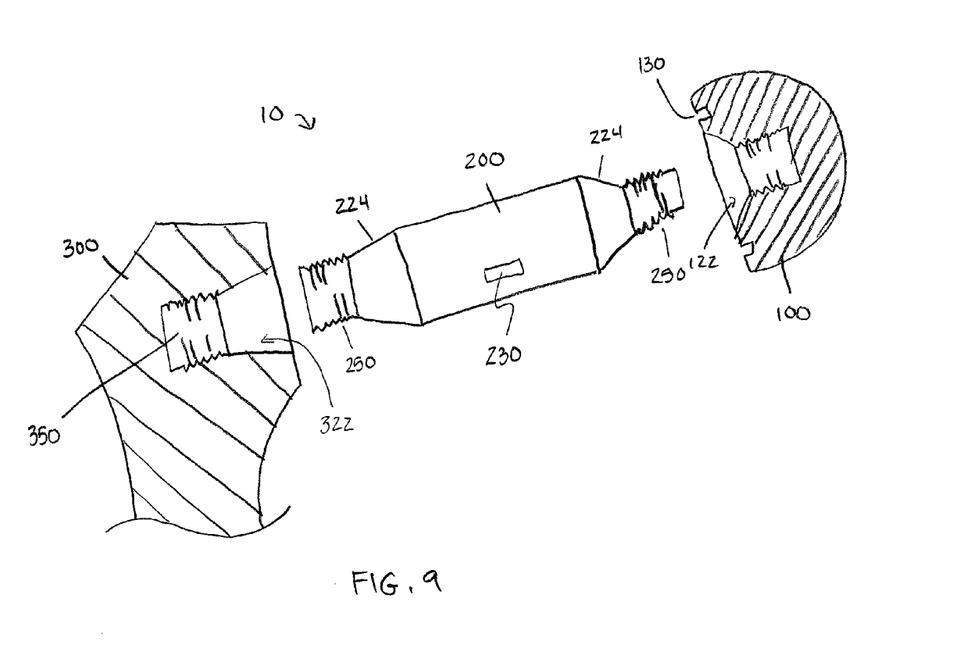
FIG. 9 illustrates a prosthetic femoral head attachable to a prosthetic femoral neck with a thread and a tapered surface interface, and a prosthetic femoral stem attachable to a prosthetic femoral neck with a thread and a tapered surface interface, in accordance with one embodiment of the present invention.

In one embodiment, as shown at FIG. 9, prosthetic femoral neck is attachable to both a prosthetic femoral head and a prosthetic femoral stem with respective threads and tapered surface interfaces.

Numerous variations and modifications of the invention will become readily apparent to those skilled in the art. Accordingly, the invention may be embodied in other specific forms without departing from its spirit or essential characteristics. The embodiments presented herein are to be considered in all respects only as illustrative and not restrictive and the scope of the invention is, therefore, indicated by the appended claims rather than by the foregoing descriptions. Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Any of the embodiments of the devices, systems, assemblies, components, methods, and/or steps can be combined with other embodiments.

What is claimed is:

1. A method of attaching a prosthetic femoral neck to a prosthetic femoral head, comprising:
   rotating a femoral neck component with respect to a femoral head component to engage a threaded interface between the femoral neck component and the femoral head component;
   engaging a tapered cone surface on a distal portion of the femoral neck component with a tapered bore surface on a bore of the femoral head component;
   lowering the temperature of at least a portion of the femoral neck component;
   permitting the temperature of the portion of the femoral neck component to rise such that an interference fit between the femoral neck component and the femoral head component is increased
   lowering the temperature of at least a portion of a third component;
   interconnecting the portion of the third component with a portion of at least one of the femoral neck component and the femoral stem component in a second interference fit; and
   permitting the temperature of the portion of the third component to rise such that the interference fit between the third component and one of the femoral neck component and the femoral stem component is increased.

2. The method of claim 1, further comprising locking the threaded interface femoral head component.

3. The method of claim 1, wherein the rotating to engage the threaded interface aligns the engagement of the femoral neck component and the femoral head component.

4. The method of claim 1, wherein the rotating to engage the threaded interface controls a taper engagement force between the femoral neck component and the femoral head component.

5. The method of claim 1, wherein the rotating step is configured to reduce any of the group consisting of fretting, corrosion, and material release from the femoral neck component and the femoral head component.

6. A method of attaching a prosthetic femoral neck to a prosthetic femoral stem, comprising:
   rotating a femoral neck component with respect to a femoral stem component to engage a threaded interface between the femoral neck component and the femoral stem component;
   engaging a tapered cone surface on a distal portion of the femoral neck component with a tapered bore surface on a bore of the femoral stem component;
   lowering the temperature of at least a portion of the femoral neck component;
   permitting the temperature of the portion of the femoral neck component to rise such that an interference fit between the femoral neck component and the femoral stem component is increased;
   lowering the temperature of at least a portion of a third component;
   interconnecting the portion of the third component with a portion of at least one of the femoral neck component and the femoral stem component in a second interference fit; and
   permitting the temperature of the portion of the third component to rise such that the interference fit between the third component and the femoral neck component is increased.

7. The method of claim 6, further comprising locking the threaded interface.

8. The method of claim 7, wherein the rotating to engage the threaded interface controls a taper engagement force between the femoral neck component and the femoral stem component.

9. The method of claim 6, wherein the rotating to engage the threaded interface aligns the engagement of the femoral neck component and the femoral stem component.

10. The method of claim 6, wherein the rotating step is configured to reduce any of the group consisting of fretting, corrosion, and material release from the femoral neck component and the femoral stem component.

\* \* \* \* \*